United States Patent [19]

Mitchell et al.

[11] Patent Number: 5,641,722
[45] Date of Patent: Jun. 24, 1997

[54] HIGH PERFORMANCE VPO CATALYST AND PROCESS OF PREPARATION THEREOF

[75] Inventors: Scott F. Mitchell, St. Charles; Robert A. Keppel, Chesterfield; Michael J. Mummey, Foley, all of Mo.

[73] Assignee: Huntsman Petrochemical Corporation, Salt Lake City, Utah

[21] Appl. No.: 306,489

[22] Filed: Sep. 15, 1994

[51] Int. Cl.$^6$ ................................................. B01J 27/198
[52] U.S. Cl. ................................. 502/209; 502/353
[58] Field of Search ............................. 502/209, 353

[56] References Cited

U.S. PATENT DOCUMENTS

| | | | |
|---|---|---|---|
| 3,864,280 | 2/1975 | Schneider | 252/435 |
| 4,092,269 | 5/1978 | Mount et al. | 252/435 |
| 4,116,868 | 9/1978 | Mount et al. | 252/428 |
| 4,162,285 | 7/1979 | Tannbashi | 264/66 |
| 4,187,235 | 2/1980 | Katsumoto et al. | 260/346 |
| 4,251,390 | 2/1981 | Barone | 252/435 |
| 4,315,864 | 2/1982 | Bremer et al. | 260/346 |
| 4,328,162 | 5/1982 | Hyatt et al. | 260/397 |
| 4,333,853 | 6/1982 | Milberger et al. | 252/435 |
| 4,386,215 | 5/1983 | Mount et al. | 549/259 |
| 4,400,561 | 8/1983 | Mitchell et al. | 568/902 |
| 4,454,245 | 6/1984 | Robinson et al. | 502/209 |
| 4,455,388 | 6/1984 | Robinson et al. | 502/209 |
| 4,520,127 | 5/1985 | Otake et al. | 502/209 |
| 4,567,158 | 1/1986 | Wrobleski et al. | 502/209 |
| 4,632,915 | 12/1986 | Keppel et al. | 502/209 |
| 4,632,916 | 12/1986 | Bither, Jr. | 502/209 |
| 4,639,530 | 1/1987 | Moorehead | 549/260 |
| 4,699,985 | 10/1987 | Bither, Jr. | 549/260 |
| 4,713,464 | 12/1987 | Fumagalli et al. | 549/259 |
| 4,784,981 | 11/1988 | Alpers et al. | 502/209 |
| 4,801,567 | 1/1989 | Moorehead | 502/77 |
| 5,137,860 | 8/1992 | Ebner et al. | 502/209 |
| 5,275,996 | 1/1994 | Andrews et al. | 502/209 |

FOREIGN PATENT DOCUMENTS

| | | |
|---|---|---|
| 0 003 431 | 1/1978 | European Pat. Off. . |
| 0 039 537 | 5/1980 | European Pat. Off. . |
| 0 151 912 | 12/1983 | European Pat. Off. . |
| 0 215 553 | 7/1985 | European Pat. Off. . |
| 0 384 749 | 2/1989 | European Pat. Off. . |

*Primary Examiner*—Shrive Beck
*Assistant Examiner*—Timothy H. Meeks
*Attorney, Agent, or Firm*—Senniger, Powers, Leavitt & Roedel

[57] ABSTRACT

An activated porous phosphorus/vanadium oxide catalyst adapted for the catalytic oxidation of a hydrocarbon to produce a carboxylic acid anhydride. The catalyst comprises a shaped body having a volume of at least about 0.02 cc, a phosphorus content of between about 1.05 and about 1.20, a B.E.T. surface area of at least about 15 $m^2/g$, an average vanadium oxidation state of between about 4.06 and about 4.3, a total pore volume of at least about 0.15 cc/g, a normalized apparent shaped body density of between about 1.0 and about 2.0 g/cc, and a crush strength of at least about 4 pounds. At least about 20% of the pore volume of the catalyst is constituted of pores having a diameter between about 0.1 and about 3.3 µM, and at least about 40% of the pore volume is constituted of pores having a diameter of less than about 0.1 µM. The catalyst is prepared by mixing a particulate phosphorus/vanadium oxide precursor with a pore modification agent to produce a modified catalyst precursor composition, forming the modified precursor composition into a predetermined shape, and removing the pore modification agent substantially at a temperature below 300° C., preferably using air as a stripping gas.

35 Claims, 12 Drawing Sheets

5,641,722

1

HIGH PERFORMANCE VPO CATALYST AND PROCESS OF PREPARATION THEREOF

BACKGROUND OF THE INVENTION

This invention relates to phosphorus/vanadium oxide catalysts useful in a process for the oxidation of hydrocarbons to dicarboxylic acid anhydrides, and more particularly to a high surface area catalyst of improved microstructure which provides high yields in such a process. The invention is also directed to a method for the preparation of the catalyst.

Numerous catalysts containing vanadium, phosphorus and oxygen (sometimes referred to as mixed oxides of vanadium and phosphorus), substantially in the form of vanadyl pyrophosphate, optionally containing a promoter component, are disclosed in the prior art as being useful for the conversion of various hydrocarbon feed stocks to maleic anhydride. In general, such catalysts wherein the valence of the vanadium is less than +5, usually between about +3.8 and about +4.8, are considered particularly well suited for the production of maleic anhydride from hydrocarbons having at least four carbon atoms in a straight chain (or cyclic structure). Typically, such catalysts also contain promoter elements or components which are considered to be present in the catalyst as oxides. Common organic feed stocks include non-aromatic hydrocarbons such as n-butane, 1- and 2-butenes, 1,3-butadiene, or mixtures thereof.

Generally, such catalysts are prepared by contacting vanadium-containing compounds, phosphorus-containing compounds, and promoter component-containing compounds (when a promoter element is desired) under conditions sufficient to reduce pentavalent vanadium to the tetravalent state and form the desired catalyst precursor comprising vanadyl hydrogen phosphate, optionally containing a promoter component. The catalyst precursor is thereafter recovered, typically in particulate form, and subjected to a variety of further conventional processing techniques to produce the active catalyst. An essential step in such further processing is calcination. Prior to calcination, the catalyst is typically formed into a shaped body such as tablet or pellet by compression in a die. A lubricant is ordinarily incorporated in the precursor composition to facilitate the tableting or pelletizing process.

In its final form, the catalyst comprises a mass of porous tablets, pellets, other shaped bodies or granules which are charged in bulk to provide the catalyst bed of a fixed bed reactor. Typically, the catalyst is charged to a tubular reactor comprising the tubes of a shell and tube heat exchanger. Hydrocarbon and oxygen are fed to the tubes, and a heat transfer fluid, such as molten salt, is circulated through the shell to remove the exothermic heat of the oxidation reaction. The porous nature of the catalyst contributes substantially to the active surface area at which the catalytic reaction takes place. However, for the internal surfaces of the catalyst body (tablets or pellets) to be utilized effectively, the feed gases, hydrocarbon and oxygen, must diffuse through the pores to reach the internal surfaces, and the reaction products must diffuse away from those surfaces and out of the catalyst body.

It is known in the art that resistance to internal diffusion in the catalyst bodies can become a rate limiting factor in the reaction. The diffusion paths can be shortened (and catalyst body external surface increased) by using relatively small catalyst granules. However, in this case better mass transfer is purchased at a sacrifice in pressure drop through the fixed bed. Thus, a need has existed in the art for a phosphorus/vanadium oxide catalyst having a microstructure such that internal diffusion resistance is minimized and productivity is enhanced at constant granule size and pressure drop.

Zazhigalov, et al, "Effect of the Pore Structure and Granule Shape of V—P—O Catalyst on the Selectivity of Oxidation of n-Butane," Zhurnal Prikladnoi Kimii, Vol. 61, No. 1, pp. 101–105 (January 1988) reports that the activity of V—P—O catalysts in the oxidation of n-butane increases with an increase in the total pore volume and macropore volume. Zazhigalov et al further describe the use of polyethylene oxide as a pore forming additive in the preparation of V—P—O catalyst to produce granules having a greater proportion of macropores. The pore builder is apparently incorporated in the catalyst precursor formulation, and later removed from the catalyst by burning it out in the calcination step. This process produces a catalyst having a proportion of macropores significantly greater than was realized without the pore builder. However, despite the previously recognized advantage of macropores, test reactor experiments show that the addition of polyethylene oxide resulted in a decrease in the efficiency of the catalyst. Zazhigalov et al. explains these results by assuming that, after burn-up of the polymer, a dense film of coke remains on the surface of the catalyst and deactivates the active centers of the catalyst. They confirmed that hypothesis by the detection of $CO_2$ that was liberated when the catalyst was heated (873° K.) in an air current.

Mount et al. U.S. Pat. No. 4,092,269 is directed to a phosphorus/vanadium oxygen catalyst prepared by reaction of phosphoric acid, phosphorus acid and vanadium pentoxide in an aqueous medium to produce a catalyst precursor, which is converted to an active catalyst by calcination. The catalyst produced contains predominantly pentavalent vanadium, generally having an average vanadium oxidation state of about +4.6 or more. The B.E.T. surface area of the Mount catalyst is about 8 $m^2/g$ or less, and the pore volume of the catalyst from pores having diameters between about 0.8 microns and about 10 microns is greater than 0.02 cc/g. Preferably, the volume constituted of pores having diameters between 1 and 5 microns is at least about 0.03 cc/go However, Mount states that catalysts having a pore volume from pores having diameters larger than about 10 microns have virtually no effect on the yield of maleic anhydride using such catalysts. Catalysts having Mount's desired fraction of 0.8 to 10 micron macropores are prepared by adding a pore modification agent to the precursor at any stage prior to calcination. Calcination of the precursor containing the pore modification agent is conducted at a temperature between about 300° and 600° C., during which substantial oxidation of tetravalent to pentavalent vanadium takes place. A lengthy list of pore modification agents is disclosed, including adipic acid, citric acid, oxalic acid, stearic acid, polyethylene glycol, polyvinyl alcohol, polyacrylic acid, cellulosic materials, monosaccharides, polysaccharides, hydrogenated vegetable oils, waxes, and gelatin. Cellulosic materials and hydrogenated vegetable oils are preferred, and methylcellulose especially preferred. The Mount et al. reference states that the yield of maleic anhydride using a phosphorus/vanadium oxide catalyst is significantly improved by controlling the pore size distribution of the finished catalyst in the ranges discussed above. In the working examples of Mount et al., the pore modification agent is removed by calcining at 380° to 500° C.

Bither U.S. Pat. No. 4,699,985 describes the preparation of a maleic anhydride catalyst in which a precursor catalyst is blended with 3 to 5% by weight of an organic pore modifying agent, and with fumed silica in an amount of 0.05 to 0.20% by weight. Upon firing of the blend, the organic pore modifying agent and the fumed silica generate a catalyst microstructure which is said to lead to enhanced production of maleic anhydride. Pore builders disclosed as suitable include organic acids, polymeric materials, cellulosic materials, monosaccharides and polysaccharides, hydrogenated vegetable oils and waxes. A preferred pore builder is Sterotex hydrogenated cottonseed oil. The pore modifying agent also serves as a lubricant in preparing shaped catalyst particles. According to the disclosure, the precursor blend is fired in a controlled manner to generate and activate the catalyst species. Precursor catalyst pellets are heated in a low flow of air at 375° to 400° C. for 1 to 6 hours, and thereafter in a more rapid flow of 1 to 1.5% n-butane in air at 450° to 490° C. for an additional 16–24 hours. In a preferred method, the shaped catalyst precursor blend is initially fired in a continuous zoned belt furnace in an air atmosphere. The temperature varies from ambient at the furnace ends to 390° to 395° C. at the center of the heated zone. Air diffuses through baffles at the ends of the furnace to replace combustion products diffusing out through vertical vents located in the heated zone of the furnace.

Methods have been developed in the art for the preparation of high surface area catalysts by reaction of vanadium pentoxide and a phosphorus compound in an organic medium. The surface area of these catalysts is generally in the range of 15 $m^2/g$ or greater as determined by the method of Brunauer, Emmett and Teller, *J. Am. Chem. Soc.*, 60, 309 (1938). Surface area as determined by this method is generally referred to in the art as "B.E.T." surface area. Methods for producing high surface area catalysts are described, for example, in U.S. Pat. Nos. 4,632,916; 4,632,915; 4,567,158; 4,333,853; 4,315,864; 4,328,162; 4,251,390; 4,187,235; and U.S. Pat. No. 3,864,280.

U.S. Pat. No. 5,137,860 describes a process for the transformation of a catalyst precursor represented by the formula:

$$VO(M)_m HPO_4 \bullet aH_2O \bullet b(P_{2/c}O) \bullet n(organics)$$

into an active catalyst represented by the formula:

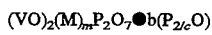

$$(VO)_2(M)_m P_2O_7 \bullet b(P_{2/c}O)$$

where M is at least one promoter element selected from the group consisting of elements from Groups IA, IB, IIA, IIB, IIIA, IIIB, IVA, IVB, VA, VB, VIA, VIB, and VIIIA of the periodic table, and mixtures thereof, m is a number from zero (0) to about 0.2, a is a number of at least about 0.5, b is a number taken to provide a P/V atom ratio of from about 1.0 to about 1.3, c is a number representing the oxidation number of phosphorus and has a value of 5, and n is a number taken to represent the weight % of intercalated organic components in the precursor. In transforming the precursor to the active catalyst, the precursor is heated in an atmosphere of air, steam, inert gas, and mixtures thereof to a temperature not greater than about 300° C. The catalyst precursor is maintained at such temperature under an atmosphere containing molecular oxygen, steam, and optionally an inert gas, the atmosphere being represented by the formula $(O)_x(H_2O)_y(IG)_z$ where IG is an inert gas and x, y, and z represent mol percentages of the $O_2$, $H_2O$, and IG components, respectively, in the molecular oxygen/steam-containing atmosphere, x having a value greater than zero (0) mol percent, y having a value greater than zero (0) mol % but less than 100 mol %, and z having a value representing the balance of the molecular oxygen/steam-containing atmosphere. The temperature is increased at a programmed rate of from about 2° C./min. to about 12° C./min. to a value effective to eliminate the water of hydration from the catalyst precursor. The temperature is then adjusted to a value greater than 350° C., but less than 550° C. and the adjusted temperature is maintained in the molecular oxygen/steam-containing atmosphere for a time effective to provide a vanadium oxidation state of from about +4.0 to about +4.5. The adjusted temperature is maintained thereafter in a non-oxidizing, steam-containing atmosphere for a time effective to complete the catalyst precursor-to-active catalyst transformation to yield the active catalyst.

Andrews et al. U.S. Pat. No. 5,275,996 describes a pore modified catalyst produced using pore modification agents similar to those of Mount U.S. Pat. No. 4,092,269. The catalyst is activated by the method of U.S. Pat. No. 5,137,860 and has a phosphorus/vanadium atom ratio of 1.05 to 1.15, a B.E.T. surface area off at least about 20 $m^2/g$, an average vanadium oxidation state of between about 4.06 and about 4.3, a total pore volume of at least about 0.15 cc/g, a normalized apparent shaped body density of between about 1.0 and about 2.0 g/cc, and a crush strength of at least about 4 pounds. At least about 5% of the pore volume of the catalyst is constituted of pores having an average diameter of at least about 0.8 microns, and at least about 4% of the pore volume is constituted of pores having an average diameter of at least about 10 microns. The pore modification agent is preferably volatilized by stripping with an inert gas, containing at least about 5% by volume water vapor, at a temperature in the range of between about 150° C. to about 250° C. After 95% to 98% of the pore builder has been removed, Andrews teaches the incorporation of up to 5% by volume, preferably no more than 2% by volume, oxygen in the stripping gas to avoid overstripping and undesirable abstraction of labile oxygens from the crystal lattice of the V—P—O precursor. During subsequent exposure to an oxygen-containing gas stream during the initial heat up phase of the activation process, the temperature is ramped from 300° to 400° C. at a rate of 2° to 12° C. per min.

SUMMARY OF THE INVENTION

Among the several objects of the present invention, therefore, may be noted the provision of an improved phosphorus/vanadium oxide catalyst effective in the catalytic oxidation of hydrocarbons, more particularly the catalytic oxidation of $C_4$ hydrocarbons to maleic anhydride; the provision of such a catalyst which is permeable to relatively rapid internal diffusion of reactant and product gases; the provision of such a catalyst which may be used to produce maleic anhydride at high productivity but low pressure drop; and the provision of a process for the preparation of such a catalyst.

Briefly, therefore, the invention is directed to an activated porous phosphorus/vanadium oxide catalyst adapted for the catalytic oxidation of a hydrocarbon to produce a carboxylic acid anhydride. The catalyst comprises a shaped body having a volume of at least 0.02 cc, a phosphorus/ vanadium atom ratio of between about 1.05 to about 1.20, a B.E.T. surface area of at least about 15 $m^2/g$, an average vanadium oxidation state of between about 4.06 and about 4.3, a total pore volume of at least about 0.15 cc/g, a normalized apparent shaped body density of between about 1.0 and about 2.0 g/cc, and a crush strength of at least about 4 pounds. At least about 20% of the pore volume of the catalyst is constituted of pores having a diameter between about 0.1 microns and about 3.3 microns, and at least about 40% of the pore volume is constituted of pores having a diameter of less than about 0.1 microns.

The invention is further directed to a process for the preparation of a phosphorus/vanadium oxide catalyst. In the process, a modified catalyst precursor composition is prepared comprising a mixture of a particulate phosphorus/vanadium oxide catalyst composition and a pore modification agent in proportion sufficient to provide a pore modification agent concentration of from about 8% to about 16% by weight. The pore modification agent is subject to vaporization, decomposition, and/or oxidation at a temperature below 300° C. without leaving a substantial residue. The precursor composition is formed into a predetermined shape under compression, thereby producing a shaped porous catalyst precursor body comprising the catalyst precursor composition and containing the pore modification agent. The catalyst precursor body is heated while passing a stripping gas thereover for removal of at least about 80% by weight of the pore modification agent from the body at temperatures not greater than about 300° C.

Other objects and features will be in part apparent and in part pointed out hereinafter.

BRIEF DESCRIPTION OF THE DRAWINGS

Corresponding reference characters indicate corresponding parts throughout the drawings.

DESCRIPTION OF THE PREFERRED EMBODIMENTS

In accordance with the invention, it has been discovered that enhanced productivity in the conversion of n-butane or other hydrocarbons to maleic anhydride is achieved by using a high surface area porous phosphorus/vanadium oxide catalyst which has been prepared using a pore builder to produce a high proportion of large pores therein. Catalysts of the invention contain primarily tetravalent vanadium, having a an average vanadium oxidation state of 4.0 to 4.5, preferably 4.06 to 4.3, and a phosphorus to vanadium atomic ratio of between about 1.05 and about 1.20. The catalysts comprise tablets, pellets or other shaped bodies having volume per shaped body of at least about 0.02 cc and a B.E.T. surface area of at least about 15 $m^2/g$. Such high surface area results from a high concentration of pores having an average pore diameter of less than about 0.05 microns. By the further presence of a high concentration of macropores having a pore diameter in the range of about 0.1 to about 3.3 microns, means are provided for rapid internal diffusion of product and reactant gases within the catalyst body. The large pores constitute flow arteries for distribution of these gases, thereby providing access of reaction gases to the active surfaces of the catalyst and egress of product gases from the finer pores of the catalyst body. This rapid exchange of gases allows maximum effective use of more of the internal surface of the tablet or pellet in the catalytic oxidation of $C_4$ hydrocarbons to maleic anhydride.

Total pore volume of the catalyst of the invention is at least about 0.15 cc/g, preferably at least about 0.18 cc/g. The catalyst possesses a uniquely advantageous combination of small pores, which present a substantial active surface for oxidation of a hydrocarbon to maleic anhydride, and larger pores, which provide access of reactants to, and egress of reaction products from, the smaller pores so that maximum effective use is made of the small pore surface area. Thus, at least about 40% of the pore volume is constituted of pores having a diameter less than about 0.1 µM, while at least about 20% of the pore volume is constituted of pores having a diameter of between about 0.1 and about 3.3 µM. In preferred embodiments of the invention, between about 40% and about 70% of the pore volume is constituted of pores having a diameter less than about 0.1 µm, between about 25% and about 60%, more preferably between about 30% and about 50%, of the pore volume is constituted of pores having a diameter between about 0.1 and about 3.3 microns, between about 10% and about 40%, more preferably between about 12% and about 30%, of the pore volume is constituted of pores having an average pore diameter between about 0.2 µM and about 2 µM, and between about 5% and about 20%, more preferably between about 7% and about 15%, of the pore volume is constituted of pores having an average pore diameter of between about 0.5 µM and about 1.2 µM.

Figure 1:
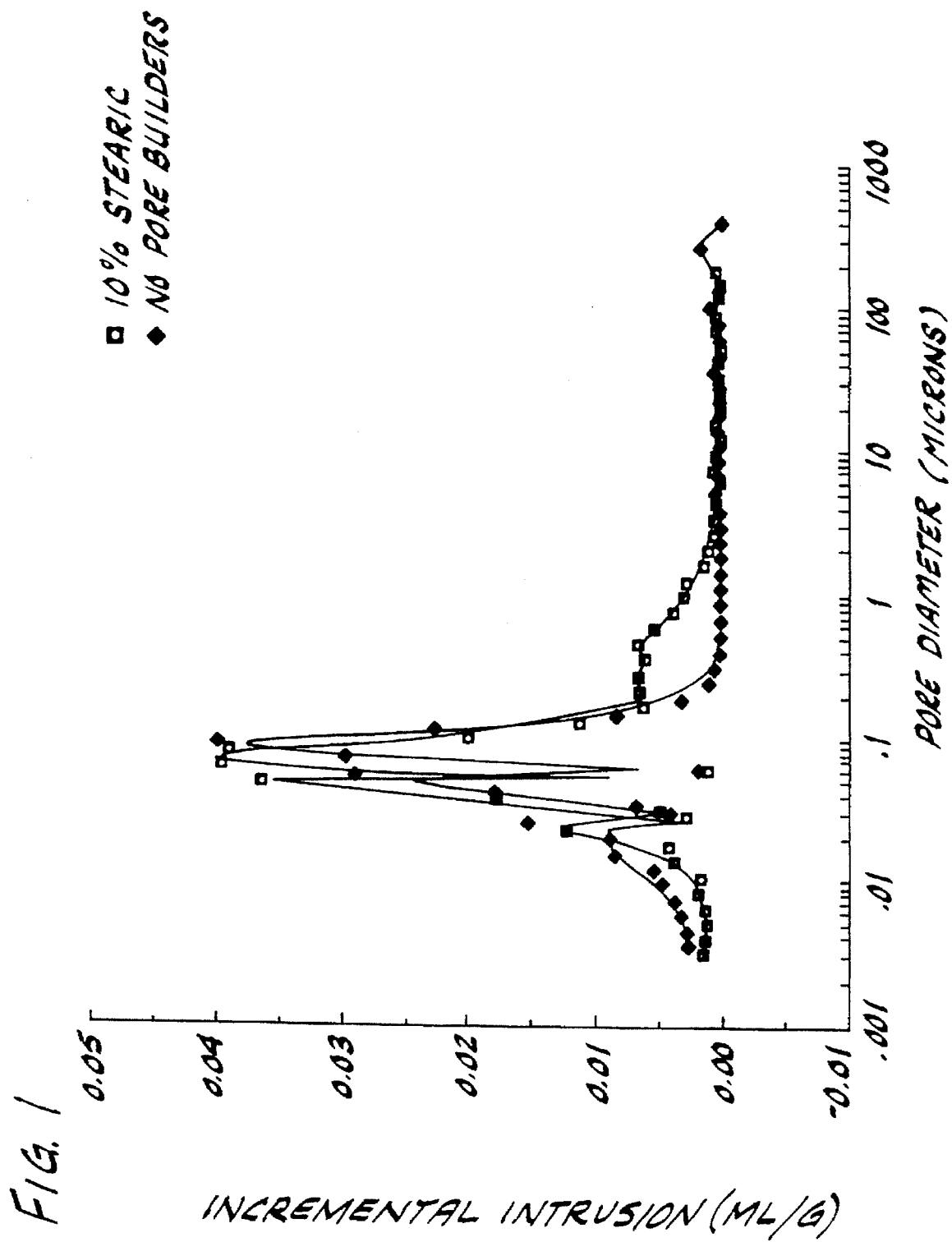
FIG. 1 is a plot comparing the distribution of pore volume as a function of pore diameter in two vanadium/phosphorus oxide catalysts prepared by ANST activation of a tabletted catalyst precursor composition, one comprising a catalyst prepared from a precursor containing no pore modification agent, the other comprising a catalyst of the invention prepared from a precursor composition containing 10% by weight stearic acid in the pores thereof.

FIG. 1 illustrates the distribution of pore volume as a function of pore diameter for the catalyst of the invention, as determined by a standard mercury porosimetry test for pore size distribution. For purposes of comparison, FIG. 1 also illustrates the pore size distribution for a catalyst prepared without use of a pore builder, but otherwise in a manner similar to that by which the catalyst of the invention was prepared. Because of the rapid internal diffusion afforded by the pore distribution within the catalyst of the invention, reactant gases can diffuse to the centers of even relatively large bodies for effective utilization of the entire internal surface thereof. This allows the catalyst to be produced in large tablets or pellets, resulting in low pressure drop through a catalyst bed without sacrificing productivity to the inaccessibility of internal surfaces. Tablets or other shaped bodies having pressure drop characteristics acceptable for commercial fixed bed reactors typically have a principal dimension of at least about ⅛", more typically ⁵⁄₃₂" to ½". Generally, therefore, the catalyst of the invention has a volume per body (as defined by the outer contours thereof) of at least about 0.02 cc, more commonly at least about 0.03 cc, and most preferably at least about 0.05 cc. Further to minimize pressure drop in a catalytic reactor containing a fixed catalyst bed comprising the shaped bodies, the shaped body preferably comprises an opening therethrough for flow of reactant and product gases when the catalyst is used in the manufacture of maleic anhydride. Advantageously, the shaped body comprise a cylinder having a bore therethrough, as illustrated, for example, in U.S. Pat. No. 4,283,307.

A substantial volume of macropores is obtained by using a pore modification agent in the preparation of the catalyst tablets or pellets. By employing relatively mild conditions in generating the macropores, the desired pore size distribution is realized without adversely affecting the activity at the active internal surfaces of the catalyst. Such advantageous results are realized by both selection of the pore modification agent and control of the conditions under which the pore modification agent is removed from the catalyst.

Catalysts of the invention have been demonstrated to afford a productivity of at least about 4 lbs. maleic anhydride per hour-ft$^3$ of catalyst; in most instances at least about 4.8 lbs. maleic anhydride per hour-ft$^3$ of catalyst, with productivities of 6 lbs. maleic anhydride per hour-ft$^3$ of catalyst being readily achievable.

Catalysts prepared by the process of the invention also exhibit crush strengths satisfactory for use in commercial reactors, for example, for the production of maleic anhydride by catalytic oxidation of n-butane. Gravity and other compaction forces tend to crush porous catalyst bodies to a powder form, which results in high pressure drop through the catalyst bed. Inadequate crush strength is generally associated with low apparent density of the catalyst bodies. Despite their high total pore volume and large proportion of macropores, the activated catalyst bodies of the invention have been found to exhibit a substantial normalized apparent shaped body density, in the range of between about 1.0 and about 2.0 g/cc, and a crush strength of at least about 4 pounds, more typically at least about 6 pounds. Normalized apparent shaped body density is the same as measured apparent density where the solid phase of the catalyst is entirely constituted of phosphorus/vanadium oxide catalyst. Where the solid phase contains a foreign material such as, for example, a particulate iron aggregate, the normalized apparent density is determined by adjusting the measured apparent density for the weight fraction of VPO in the catalyst body. Thus, if:

$a_n$=the normalized apparent body density $a_m$=the measured apparent body density x=the weight fraction VPO in the catalyst body then:

$a_n = a_m x$

Where no aggregate is present, the normalized (and measured) apparent body density is between about 1.25 and about 2.0 g/cc.

In the process of the invention, a modified catalyst precursor composition is prepared comprising a mixture of a particulate phosphorus/vanadium oxide catalyst precursor composition and a pore modification agent which is subject to removal from the catalyst after tableting or pelletizing. The pore modification agent should be subject to removal under mild conditions from the catalyst precursor body without undergoing an exothermic oxidation that adversely affects the VPO crystal structure or composition. More particularly, the pore modification agent should be removable without exposing the precursor composition to an exotherm of such severity as to cause either substantial reduction of the vanadium oxidation state or premature or uncontrollably rapid dehydration of the VPO precursor. To facilitate its removal under relatively mild conditions, the pore modification agent should be subject to vaporization, decomposition or oxidation at temperatures below 300° C. and without leaving a carbon, ash, or other residue so great as to create a substantial exotherm during the subsequent catalyst activation process. In particular, it is essential that the mechanism of removal of the pore modification agent be substantially quantitative without generating an exotherm during the removal process, whether due to decomposition or reaction with the atmosphere in which removal takes place, which would heat the catalyst precursor composition above 300° C. for more than about 20 minutes.

A preferred type of pore modification agent is thermally stable and has a substantial vapor pressure at a temperature below 300° C. It is particularly preferred that the pore modification agent have a vapor pressure of at least about 1 mm Hg at a temperature between about 150° C. and about 250° C., more preferably between about 150° C. and about 200° C.

Preferably, the pore builder has a relatively high melting point, e.g. greater than 60° C., so that it does not melt during compression of the catalyst precursor into a slug, tablet or pellet. It is also preferred that the pore builder comprise a relatively pure material rather than a mixture, so that lower melting components are not expressed as liquids under compression during formation of slugs or tablets. In the case of fatty acids, for example, it is known that lower melting components of fatty acid mixtures can be removed as liquids by pressing. If this phenomenon occurs during slug or tablet compression, the flow of liquid may disturb the pore structure and produce an undesirable distribution of pore volume as a function of pore diameter.

Particularly advantageous are pore modification agents which have a significant vapor pressure at temperatures below their melting points, so that they can be removed by sublimination into a carrier gas.

For example, the pore modification agent may be a fatty acid corresponding to the formula $CH_3(CH_2)_xCOOH$ where x>8 such as stearic acid (x=16), palmitic acid (x=14), lauric acid (x=10), myristic acid (x=12), esters of such acids and amides or other functionalized forms of such acids, for example, stearamide $(CH_3(CH_2)_{16}CONH_2)$. Suitable esters may include methyl esters as well as glycerides such as stearin (glycerol tristearate). Mixtures of fatty acids can be used, but substantially pure acids, particularly stearic, generally perform better than mixtures. While fatty acids and fatty acid derivatives are generally preferred, other compositions which meet the functional requirements discussed above are also suitable for use as pore modification agents (pore builders).

Other preferred pore modification agents include polynuclear organic compounds such as naphthalene. Naphthalene melts at about 80° C. and has an appreciable vapor pressure at temperatures below 175° C. Moreover, because it lacks both functional groups and polarity, it is not strongly adsorbed, by either physisorption or chemisorption, to the catalyst precursor composition in the catalyst precursor body. Accordingly, quantitative removal of naphthalene is readily achieved under quite mild removal conditions.

A modified catalyst precursor composition is prepared by mixing the pore builder in particulate form with a particulate precursor composition which contains oxides of vanadium and phosphorus. Preferably, the modified precursor composition contains between about 6% and about 16%, preferably between about 8% and about 12%, by weight of pore builder. Preferably, a lubricity agent is also included in the mix, e.g., between about 2% and about 6% by weight graphite. This composition is then formed under compression into a tablet or other predetermined shape. Mixing is better and tablet integrity enhanced if the mean particle diameter of the pore builder approximates the mean particle diameter of the precursor composition, at least within about two orders of magnitude. Typically, vanadium/phosphorus oxide precursor particles have a mean diameter in the range of between about 20 to 200 microns, most often in the range of between about 50 and 150 microns. It is generally preferred that the mean particle diameter of the pore builder be between about 10 and about 500 microns, more preferably between about 30 and about 90 microns, most preferably about 40 to about 50 μM.

Figure 7:
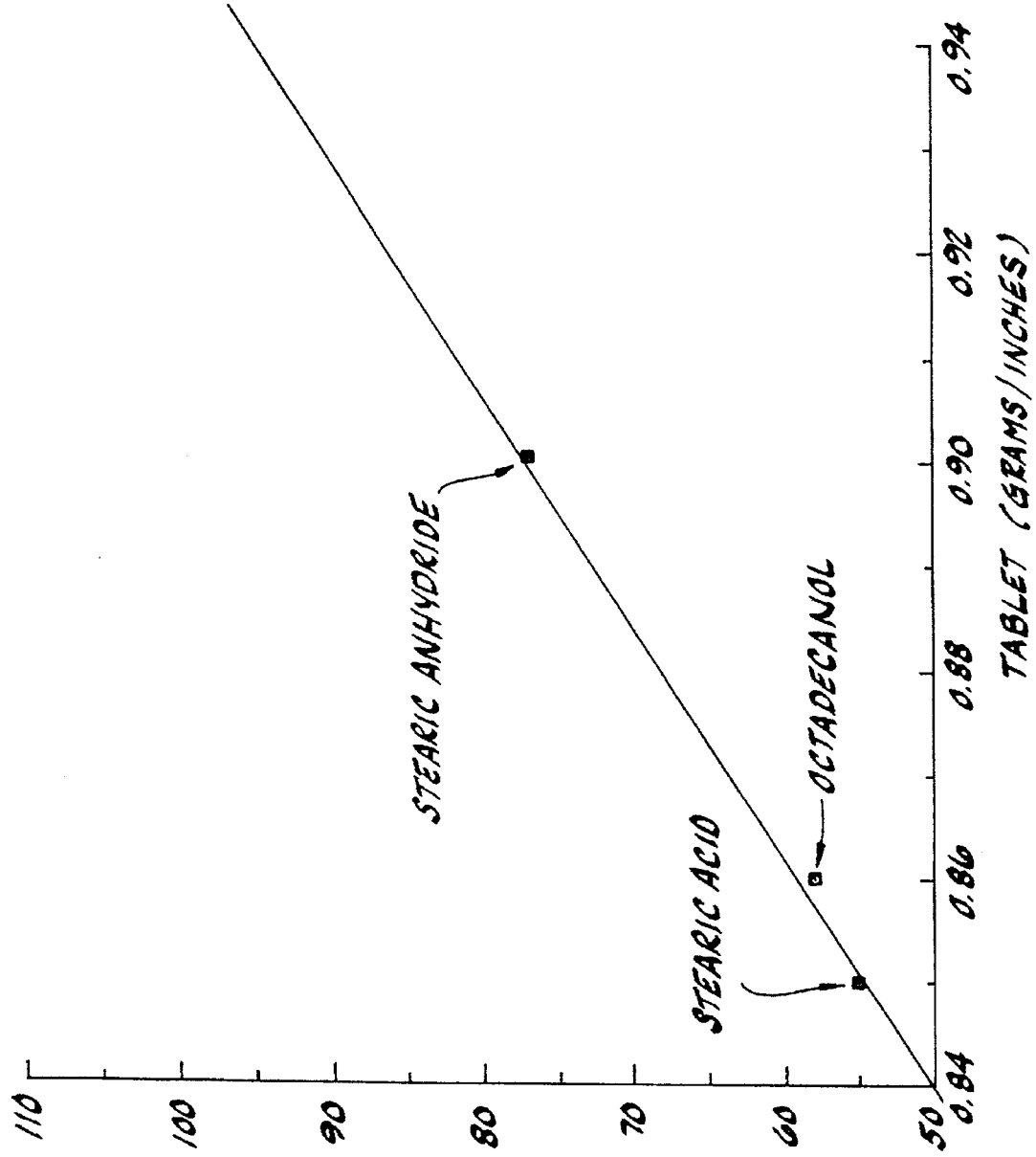
FIG. 7 is a plot illustrating a correlation between the tabletting pressure at which liquid is extruded from various pore modification agents and the melting point exhibited by the pore modification agents in the absence of compressive force.
Figure 8:
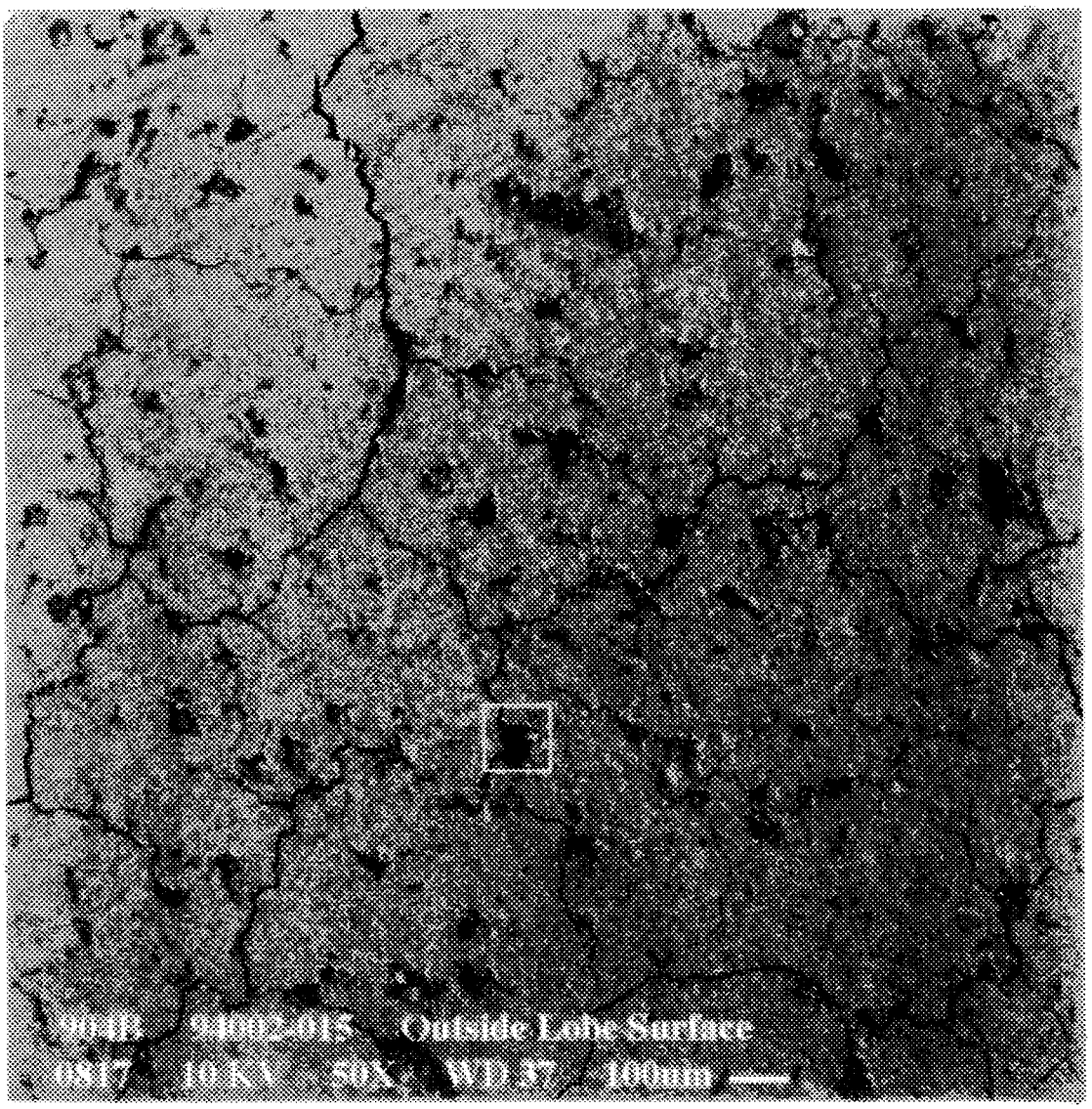
FIGS. 8 to 12 are external photomicrographs of catalyst tablets of the invention showing the incidence of surface holes communicating with the interior of the tablet.
Figure 9:
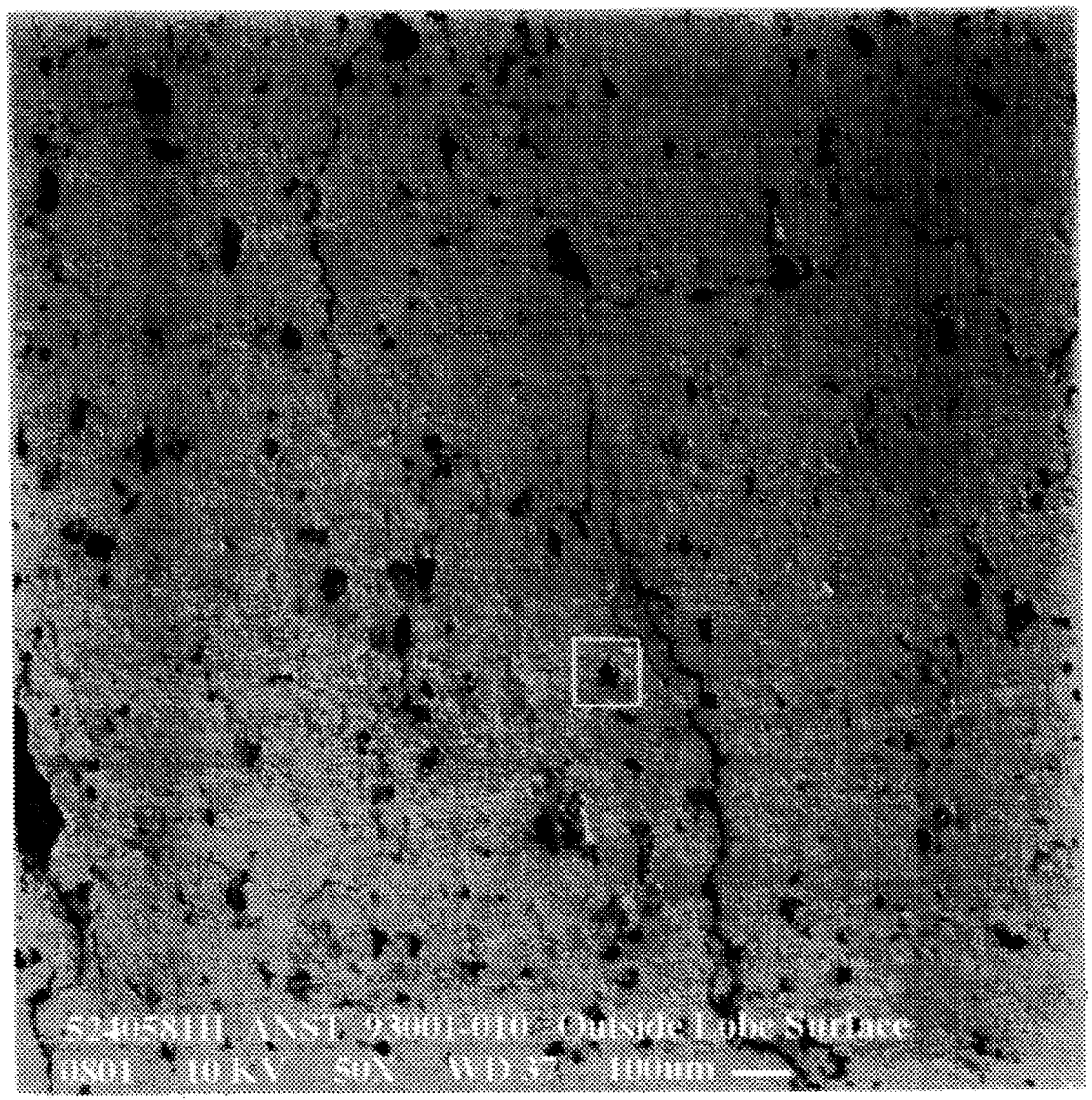
Figure 10:
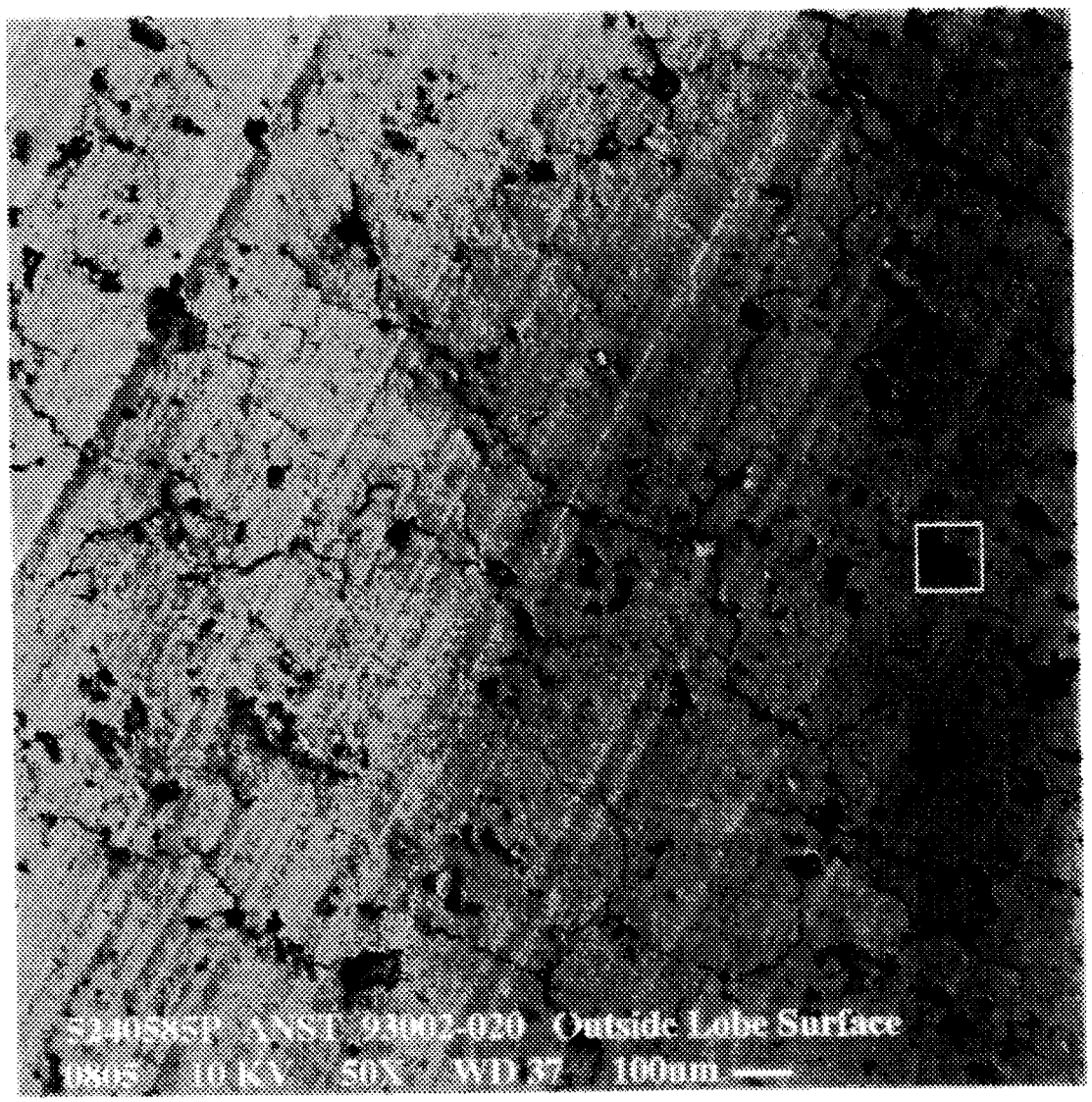
Figure 11:
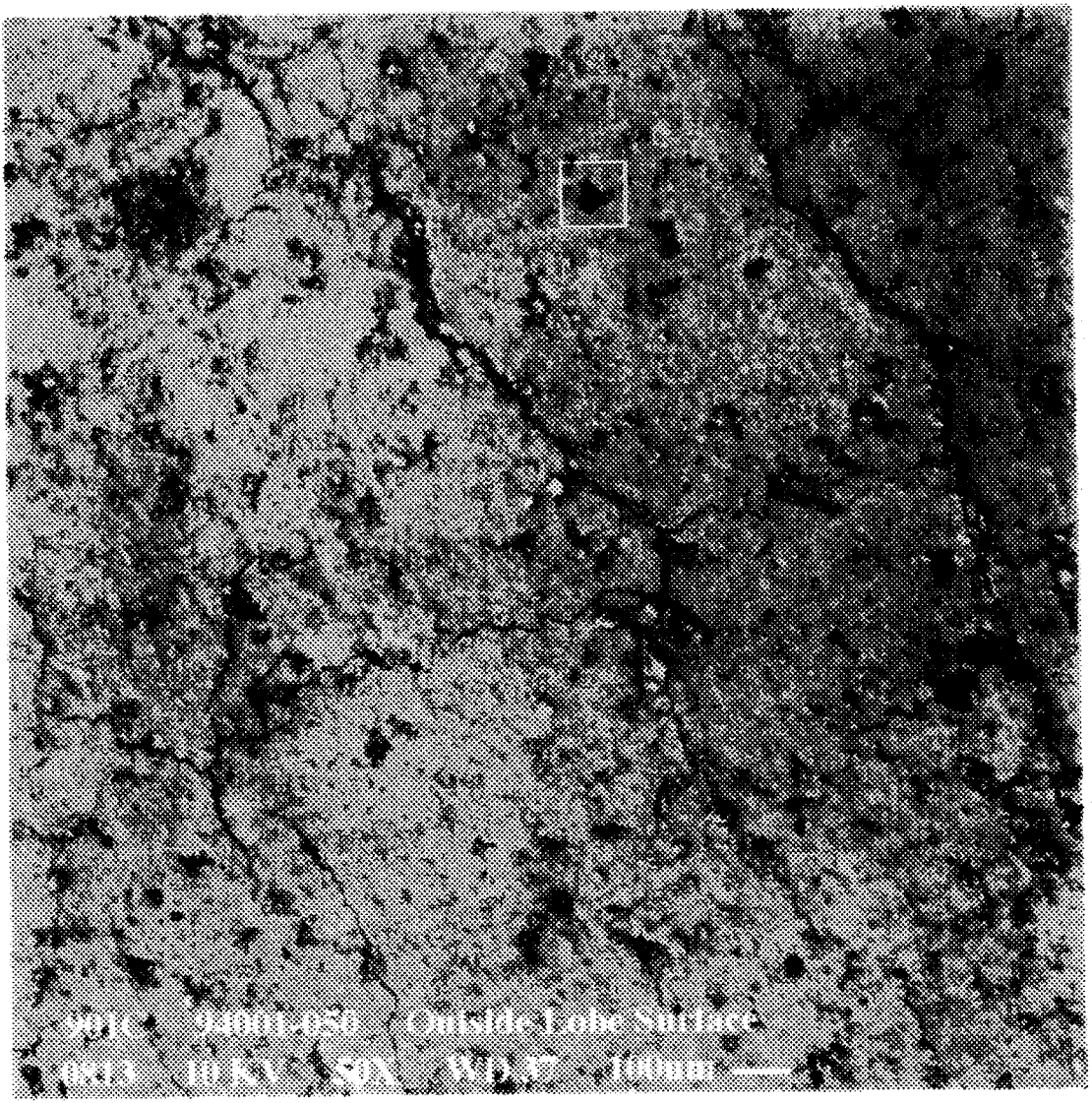
Figure 12:
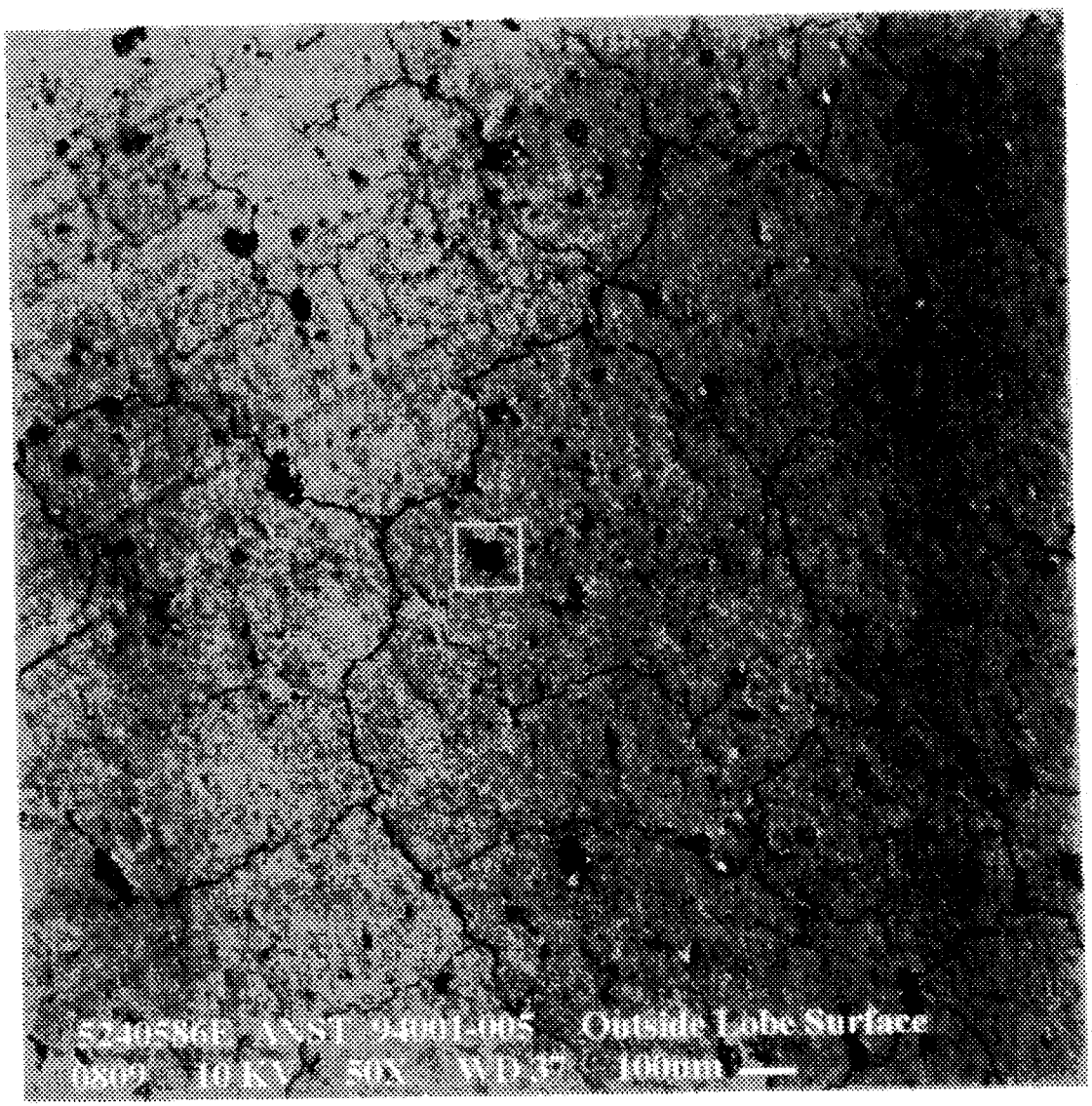

Although the particulate mixture of vanadium/phosphorus oxide precursor and pore builder can be formed directly into a precursor body which is heat treated for activation, a preferred method involves a preliminary slugging and granulation step. Thus, the modified precursor mixture is compressed to produce a slug of material, for example, in the form of a cylinder, the slug is then granulated, and the granulated composition is compressed in a die to form the tablet, pellet or other shaped precursor catalyst body. Where a fatty acid pore builder such as stearic acid is used, the slug is preferably compressed to a density of between about 1.40 and about 1.50 g/cc. Compressing to significantly higher densities may result in undesired expression of liquid phase from the fatty acid pore builder, which may cause a change in the number and size distribution of pore builder particles and in turn have a detrimental effect on the porosity of the final catalyst product. The tolerable degree of compression may be generally correlated with the pore builder's melting point in the absence of compression. FIG. 7 illustrates this relationship for a number of exemplary pore modification agents. Expression of liquid is indicated for combinations of melt point and tablet compression whose co-ordinates fall to the right of and below the solid line of FIG. 7, while expression of liquid is avoided for combinations of normal melting point and tablet compression whose co-ordinates fall to the left and above the solid line.

Granulation of the slug may be carried out by the mechanical action of mill knives operated in conjunction with a retaining screen having holes which pass the desired size granule. Preferably the granules are on the order of 200 μM to 1 mm in size, as produced by passage through a screen having 1/16" to 1/8", preferably about 3/32" holes. The tablet or other shaped body formed by compression of these granules comprises a structure of mixed particulate phosphorus/vanadium oxide structure and particulate pore builder. The shaped precursor body has a minimum principal dimension of at least about 1/8", preferably 5/32" to 1/2", and thus a volume per catalyst body of at least 0.02 cc, more preferably at least about 0.03 cc, more preferably at least about 0.05 cc.

Figure 4:
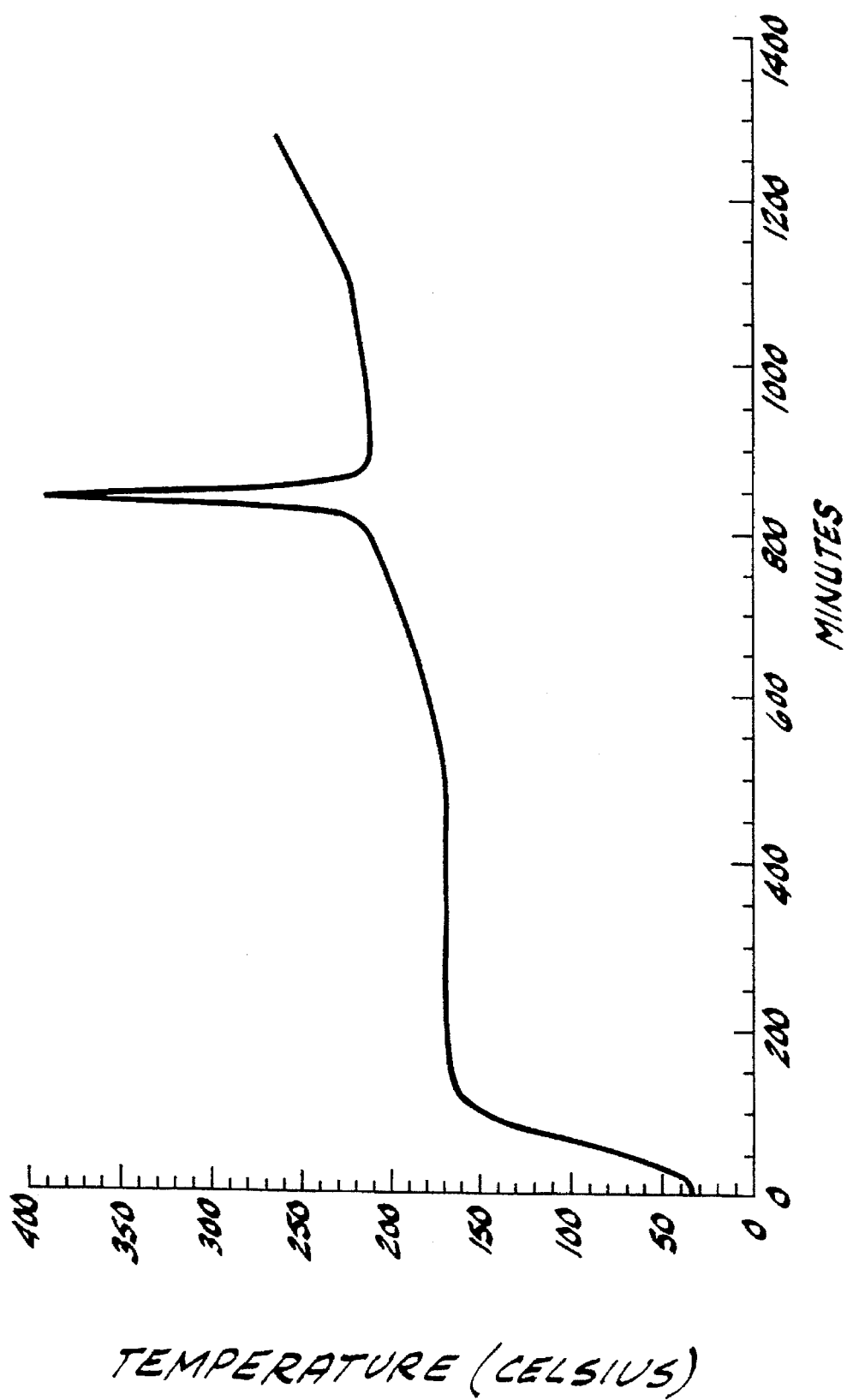
FIG. 4 is a copy of a temperature recording chart illustrating an excessive exotherm in the removal of pore builder, which resulted in the formation of a catalyst having less than desired activity.
Figure 5:
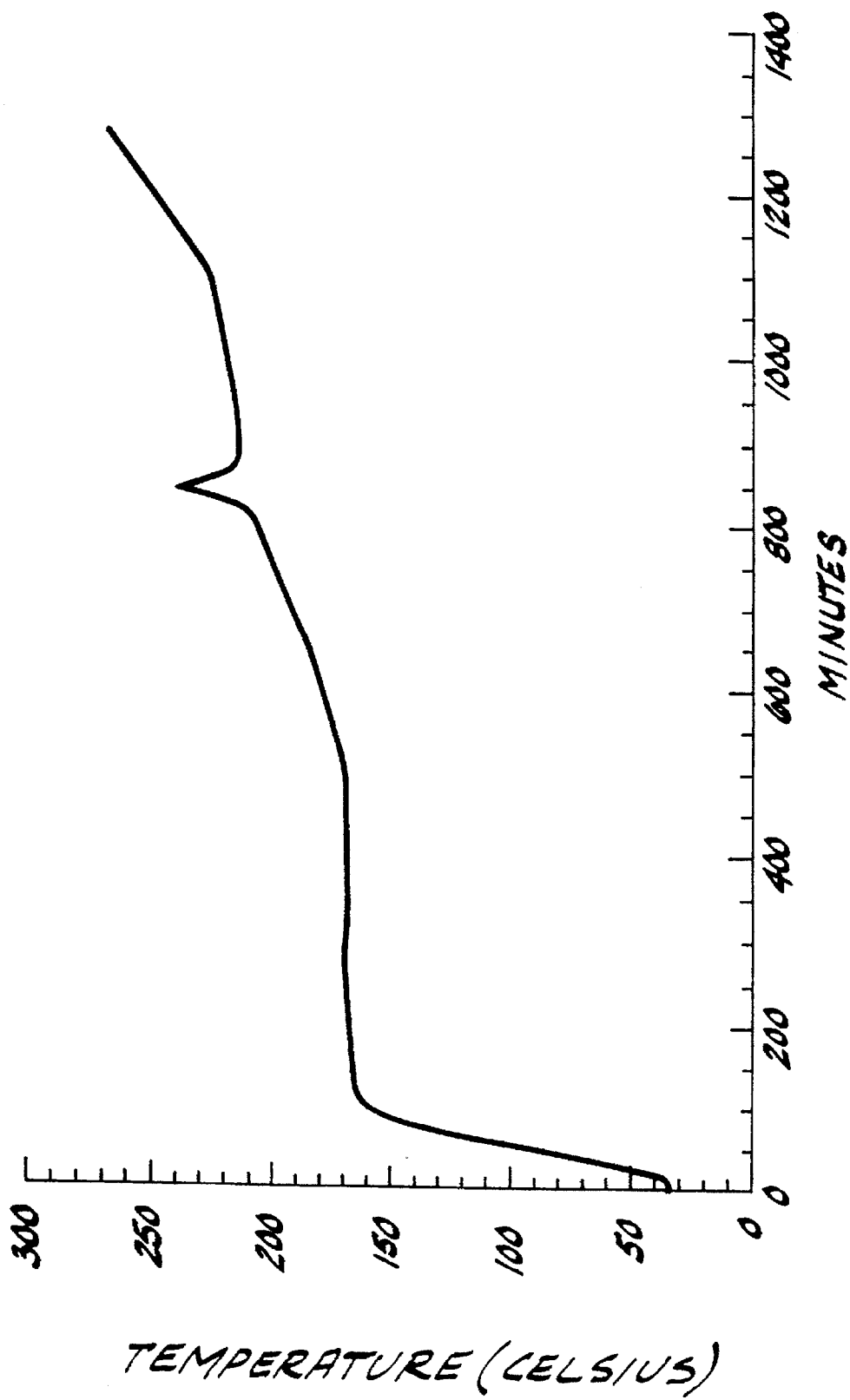
FIG. 5 is a copy of a temperature recording chart illustrating a tolerable temperature excursion in removal of pore modification agent in accordance with the process of the invention.

The tablets or other shaped precursor bodies are heated under conditions effective for removal of the pore builder from the bodies without causing an exotherm sufficient to result in excessive premature dehydration or reduction of the vanadium/phosphorus oxide precursor composition. A stripping gas is caused to flow over the shaped bodies to provide a driving force for mass transfer and to carry away the pore builder volatilized by heating. A variety of conditions can be utilized in removal of the pore builder, depending in significant part on its nature. Generally, it is preferred that the conditions be controlled so that the precursor bodies are not heated to a temperature higher than about 275° C., more preferably not higher than about 255° C. However, brief excursions to higher temperatures can be tolerated so long as neither excessive dehydration nor significant reduction is suffered. In most systems, dehydration is not excessive if the temperature does not rise to more than about 300° C. for more than about 5 to about 20 minutes. FIG. 5 illustrates a modest exotherm of the type that can be tolerated during removal of pore builder. By contrast, FIG. 4 illustrates an excessive exotherm which damages the catalyst structure.

Where the pore builder has a melting point significantly lower than the temperature at which it is removed, the precursor bodies are preferably heated to a temperature above the melting point but below the lowest temperature at which the pore builder is subject to substantial thermal degradation or oxidation by the catalyst precursor or components of the atmosphere to which the shaped body is exposed during heating. Preferably, the shaped body is heated to a temperature at which the vapor pressure of the pore builder is above 1 mm Hg, but well below 300° C. Most of the pore builders of interest may be removed at or near atmospheric pressure by heating to a temperature in the range of between about 150° C. and about 250° C. Where the pore builder has a vapor pressure of <1 mm Hg in the range of between about 150° C. to about 200° C., the shaped body is preferably heated, at gradually increasing temperature, to a terminal temperature in the range of between about 200° C. and about 250° C. The stripping gas preferably flows over the catalyst body at a velocity of at least about 25 cm/sec., more preferably between about 50 and about 75 cm/sec. Satisfactory removal of pore builder can be realized over a wide range of pressure, including atmospheric and above. A pressure slightly below atmospheric is preferred.

In order to prevent excessive dehydration of the VPO structure, it is important not only to avoid excessive exotherms that can result from oxidation of the pore builder with oxygen from the stripping gas when the catalyst precursor is heated too fast, but also to remove as much pore builder as possible at relatively low temperature, below the temperature at which oxidation of the pore builder may result from abstraction of oxygen from the VPO catalyst precursor structure. The latter reaction is a particular risk towards the end of the pore builder removal step, at the relatively high temperatures that may be required for lowering the concentration of residual pore builder to a level at which no serious exotherm is experienced in the subsequent catalyst activation stage. Moreover, fairly lengthy exposure to such temperatures may be necessary to eliminate residual pore builder to the extent required for the activation step, without generating an exotherm in the removal step by heating too rapidly. Thus, for example, where the shaped precursor bodies need to be heated to a temperature of 240° C. for removal of residual pore builder by stripping, they are exposed to potential dehydration and reduction not only during the approach to 240° C. but also during the several hours typically required to cool to a temperature below about 150° C. At such temperatures, if the amount of residual pore builder remains too high, the catalyst precursor structure is subject to both dehydration and reduction due to reaction of the pore builder with oxygen abstracted from the crystal VPO lattice. Moreover, where air or other oxygen containing gas is used as the stripping gas, and a substantial exotherm is experienced, the temperature of the VPO precursor may rise so high that once the pore builder has burned off, the catalyst structure becomes oxidized by reaction with oxygen in the stripping air, leading to final vanadium oxidation state well above the desired range. Thus, as discussed in more detail below, the bulk of the pore builder is preferably removed at a temperature below the temperature at which it may be subject to rapid oxidation.

It is also important to achieve substantially complete removal of the pore builder before heat treatment of the precursor bodies to produce activated catalyst bodies. When exposed to oxygen during the subsequent heat treatment for activation, residual pore builder may oxidize at an excessive rate, causing an excessive exotherm in that operation which may interfere with the conditions of the heat treatment. Thus, for example, when using the preferred method of activation as described below, it is important that, in the range of about 300° to about 400° C., the rate of increase in the temperature of the precursor bodies is not faster than about 2° to about 12° C. per minute. If any significant residual amount of pore builder is present, an exotherm may develop which increases the heating rate of the precursor bodies to well above 12° C. per minute, even where they are heated in an oven in which the rate of increase of the air or other stripping gas temperature is well within the 2° to 12° C./min. range. Accordingly, the removal step should be continued until at least 80%, preferably at least about 85%, of the pore builder has been removed, as indicated, for example, by measured weight loss during the removal step.

Severe exotherms can also be experienced in the pore builder removal step, so that the rate of temperature increase must be carefully controlled in that step as well. Many pore builder materials are subject to uncontrolled oxidation if the precursor bodies are heated too rapidly, especially at temperatures in the upper portion of the range in which pore builder is removed. Rapid oxidation may result from abstraction of oxygen from the crystal lattice, but may be much more severe where air is used as the stripping gas. It has been observed that the precursor bodies can reach temperatures as high as 600° C., essentially destroying the desired crystal structure of the catalyst. Even at temperatures well below 600° C., a substantial exotherm may result in excessive dehydration of the crystalline VPO structure. In the presence of air the oxidation state of the vanadium may be increased substantially above the preferred 4.06 to 4.3 range, while in the absence of air, the vanadium oxidation state may be reduce below that range. FIG. 4 illustrates an excessive exotherm of the type that may be generated in the course of pore builder removal.

The tendency to uncontrolled oxidation and generation of excessive exotherms is believed to be a function of the nature of the pore builder, the temperature and the amount of pore builder remaining in the precursor bodies at a given temperature. Thus, the heating rate may be critical. It has further been observed that certain pore builders are subject to catalytic oxidation in the presence of the VPO precursor beginning at a threshold temperature which varies with the nature of the pore builder. At this temperature, it is understood that oxygens of the VPO crystal lattice become labile and react with the pore builder. Oxygen withdrawn from the lattice by this reaction is replenished by oxygen transferred from the stripping gas. If the amount of remaining pore builder is low when the threshold ("light off") temperature is reached, catalytic oxidation provides a useful and beneficial means of substantially eliminating residual pore builder prior to high temperature heat treatment for transformation of the precursor to active catalyst. This phenomenon may provide a particular benefit when air is used as the stripping gas. In such instance, the pore builder oxidation proceeds at a controlled rate, causing neither excessive dehydration, reduction of vanadium, oxidation of vanadium, or adverse alteration of the crystal structure. However, if the amount of remaining pore builder is too great, catalytic oxidation thereof may generate an excessive exotherm. Thus, it is desirable to remove as much of the pore builder as possible at relatively low temperature.

In a preferred embodiment of the invention, therefore, the precursor bodies are initially heated at a modest rate, for example, at a rate such that their temperature increases at between about 1° C. and about 3° C. per minute to a hold temperature at or slightly lower, preferably no more than about 15° C. lower, than the light off temperature for catalytic oxidation of the pore builder in the presence of the precursor. Operation at the light off temperature is acceptable because the oxidation rate at this temperature is slow enough that the reaction heat can be readily removed by the stripping gas, and both bulk and local hot spots are avoided. The precursor bodies are then maintained at the hold temperature for a period of time during which additional amounts of pore builder are removed by evaporation. During the initial heatup and the hold period, the stripping gas serves as a heat source, and the pore builder is removed essentially by evaporation or sublimation, while oxidation is substantially avoided. After the hold period, heating of the precursor bodies is resumed at a very slow rate to the light off temperature, and beyond the light off temperature to the terminal temperature of the pore builder removal step. During the latter phase of the process, it is believed that residual pore builder is removed both by evaporation and catalytic oxidation. In this period, the stripping gas typically serves as a heat sink rather than a heat source, as is indicated by the fact that the temperature of the catalyst bodies ordinarily exceeds the temperature of the stripping gas once the light off temperature for the pore builder has been reached.

Where stearic acid is used as the pore builder, air is preferably used as the stripping gas, and the precursor bodies are heated to increase their temperature at a rate of about 1° C. to about 3° C. per minute from the initial temperature, typically ambient, to a hold temperature not greater than about 170° C., preferably about 165° C. At the velocities discussed above, the air is advantageously recirculated for conservation of energy, a fractional purge stream having a flow volume of 5% to 20% of the circulating rate being withdrawn for disposal of pore builder and pore builder oxidation products. The bodies are maintained at the hold temperature until enough pore builder has been removed so that the heat generated by subsequent catalytic oxidation does not cause an excessive exotherm. More particularly, the catalyst bodies should be maintained at the hold temperature long enough so that any exotherm in the remainder of the pore builder removal step does not exceed a maximum temperature of about 300° C. If desired, pore builder removal during the hold period is monitored by weight loss. After the hold period, heating to increase the temperature of the precursor bodies is resumed at a very gradual rate. The hold period is typically between about 1 to about 10 hours, depending on the nature of the pore builder, the initial pore builder content, and the nature and velocity of the stripping gas. At a volumetric air flow velocity of between about 0.5 and about 20, more preferably about 4 to about 10, liter/sec.-kg catalyst precursor, and a linear velocity of between about 50 and about 75 cm/sec, the hold period for stearic acid is preferably between about 1 and about 7 hours.

After the hold period, the catalyst bodies are heated at a rate effective to progressively remove residual pore builder by oxidation and/or vaporization while avoiding the generation of an excessive exotherm. The rate of removal is a function of the amount of residual pore builder and the temperature. As the temperature increases, the proportion of catalyst sites that are active for oxidation of the pore builder may be visualized as progressively increasing. At a given temperature, the rate of removal of pore builder by oxidation and/or vaporization declines as pore builder is consumed, until the concentration of residual pore builder asymptotically approaches a limiting, essentially irreducible value. Thus, to achieve progressive reduction in pore builder concentration beyond the asymptotic limit at a given temperature, the temperature must be progressively increased. However, the rate of oxidation may become uncontrollably high if the temperature is raised too high or too rapidly at a given residual pore builder concentration. It is critically important that the oxidation rate not reach the point at which local hot spots adversely alter VPO phase structure, or even reach a self-accelerating level at which reaction heat generation rate exceeds the rate of heat removal in the stripping air flowing over the precursor tablets. As a consequence, it is necessary to increase the temperature very gradually to maintain a reasonable rate of removal of residual pore builder while avoiding an excessive exotherm. It has been found that, as the pore builder concentration decreases, it becomes feasible to moderately accelerate the rate of heating until a terminal temperature is reached at which the asymptotic concentration of residual pore builder is low enough so that an excessive exotherm is avoided in the subsequent catalyst activation step.

The exact time/temperature schedule may vary with such parameters as the identity of the pore builder, the stripping air flow velocity, the size and shape of the precursor tablets, the surface to volume ratio of the bed of catalyst bodies in the pore builder removal oven, and the total weight of catalyst precursor bodies relative to the volumetric air flow in the oven. Typically, however, the precursor bodies are heated very slowly, for example, from about 0.5° C. to about 3° C. per hour, preferably about 1° C. to about 2° C. per hour, to a temperature in the range of about 15° to 40° C. above the hold temperature, and thereafter at a rate increasing to 10° to 40° C. per hour, preferably about 15° to about 25° C. per hour, at temperatures ranging from around 200° C. to the terminal temperature (240° to 260° C. in the case of stearic acid). Thereafter, the precursor bodies are cooled to ambient temperature, preferably in about 0.5 to 2 hours. The precise temperature schedule is controlled so that the vanadium oxidation state is not reduced to below 3.8. For example, a large batch of precursor bodies containing a stearic acid pore builder may be heated on the following schedule:

| | |
|---|---|
| ambient to 170° C. | 1 hour |
| 170° C. hold | 2 hours |
| 170° C. to 185° C. | 15 hours |
| 185° C. to 199° C. | 7 hours |
| 199° C. to 255° C. | 2 hours |
| cool to ambient | 2 hours |

A smaller batch may be treated on a somewhat more aggressive schedule, for example

| | |
|---|---|
| ambient to 165° C. | 1 hour |
| 165° C. hold | 2 hours |
| 165° C. to 199° C. | 17 hours |
| 199° C. to 255° C. | 2 hours |
| cool to ambient | 2 hours |

The entire cycle has been found to extend for 15 to 35 hours, optimally 23 to 28 hours.

Removal of pore builder using air as the stripping gas, and following the temperature schedule outlined above, has been found to avoid the problem referred to as "overstripping" in Andrews U.S. Pat. No. 5,275,996. Whether overstripping results from an excessively reducing atmosphere, from oxygen abstraction resulting from bonding between the VPO substrate and carboxyl groups of a fatty acid pore builder, thermally initiated oxygen abstraction reactions, or both, it has been found that this problem is avoided in the process of the present invention wherein the heating rates are very strictly controlled and air is used as the stripping gas.

By use of air as a stripping gas under the controlled temperature conditions of the invention, even non-volatile pore builders such as methyl cellulose may be effectively used without adverse effect on the final properties of the catalyst. According to the methods of the prior art, it was necessary to burn out such non-volatile pore builders in a fashion which resulted in an excessive exotherm. More specifically, catalyst bodies containing cellulosic type pore builders were heated to rather elevated temperatures in the presence of air, causing decomposition of the pore builder into volatile fragments which were then burned in the air, causing the temperature of the catalyst body to rise far above 300° C., with consequently excessive and premature dehydration. However, by stripping with dilute oxygen-containing gas under conditions below the flammable range, cellulosic pore builders can be entirely removed at temperatures substantially below 300° C. without excessive dehydration or other adverse effect on the precursor crystal lattice.

As indicated, brief temperature excursions as high as 300° C. may be tolerated if the energy absorbed by the precursor body is not such as to cause excessive dehydration during the removal step.

Where the pore builder comprises a relatively volatile compound such as naphthalene, or other polynuclear organic which is free of polarity or functional groups that would generate high energy bonds with the precursor substrate, it may be removed by stripping at temperatures, below about 170° C., at which the oxygen atoms of the precursor crystal lattice are essentially non-labile and the vanadium is not subject to reduction in its oxidation state. Where the pore builder is removable at such modest temperatures, it may not be necessary to heat to the threshold temperature at which catalytic oxidation of the pore builder is initiated in the presence of the catalyst precursor. However, provided that the substantial bulk of the pore builder is removed by evaporation below the light off temperature, catalytic oxidation may be relied on to remove residual pore builder.

Regardless of which of the above described methods is used, the pore builder is removed from the shaped porous body, leaving a porous, gas-permeable structure containing a substantial fraction of macropores, as discussed above. When the pore builder is removed using the extended heating cycles described hereinabove, any residue of carbon, ash or adsorbed organic species at the internal surfaces of the catalyst is reduced to a practical minimum. Thus, when the precursor is subsequently transformed into active catalyst at temperatures in excess of 300° C., the highest feasible catalyst activity is realized. More particularly, the catalyst surfaces are not exposed to uncontrolled exothermic temperature excursions which may otherwise cause the catalyst temperature to rise more rapidly than about 2° to 12° C. per minute during the ramp heating from 300° to 400° C. as described in more detail hereinbelow.

Where a pore builder is burned out of a catalyst tablet by previously known methods, the internal surfaces are exposed to combustion temperatures, which are substantially in excess of the temperatures at which transformation of the catalyst precursor to active catalyst is effectively conducted. By contrast, in the process of the invention, the benefit of a substantial distribution of macropores is achieved, while the adverse effect of carbon deposits, physisorbed or chemisorbed organic species, or exposure of the pore surfaces to excessive temperatures, is avoided. Residual carbon or organic material may not be entirely eliminated, but the residual amount per unit surface area is small enough that, by careful control of the heating rate during the catalyst activation step, the residual carbonaceous material is oxidized at rate which does not cause a substantial exotherm, and does not result in either reduction of vanadium, untoward dehydration of the VPO precursor, loss of effective B.E.T. surface area, or adverse effect on the VPO crystal structure.

Figure 2:
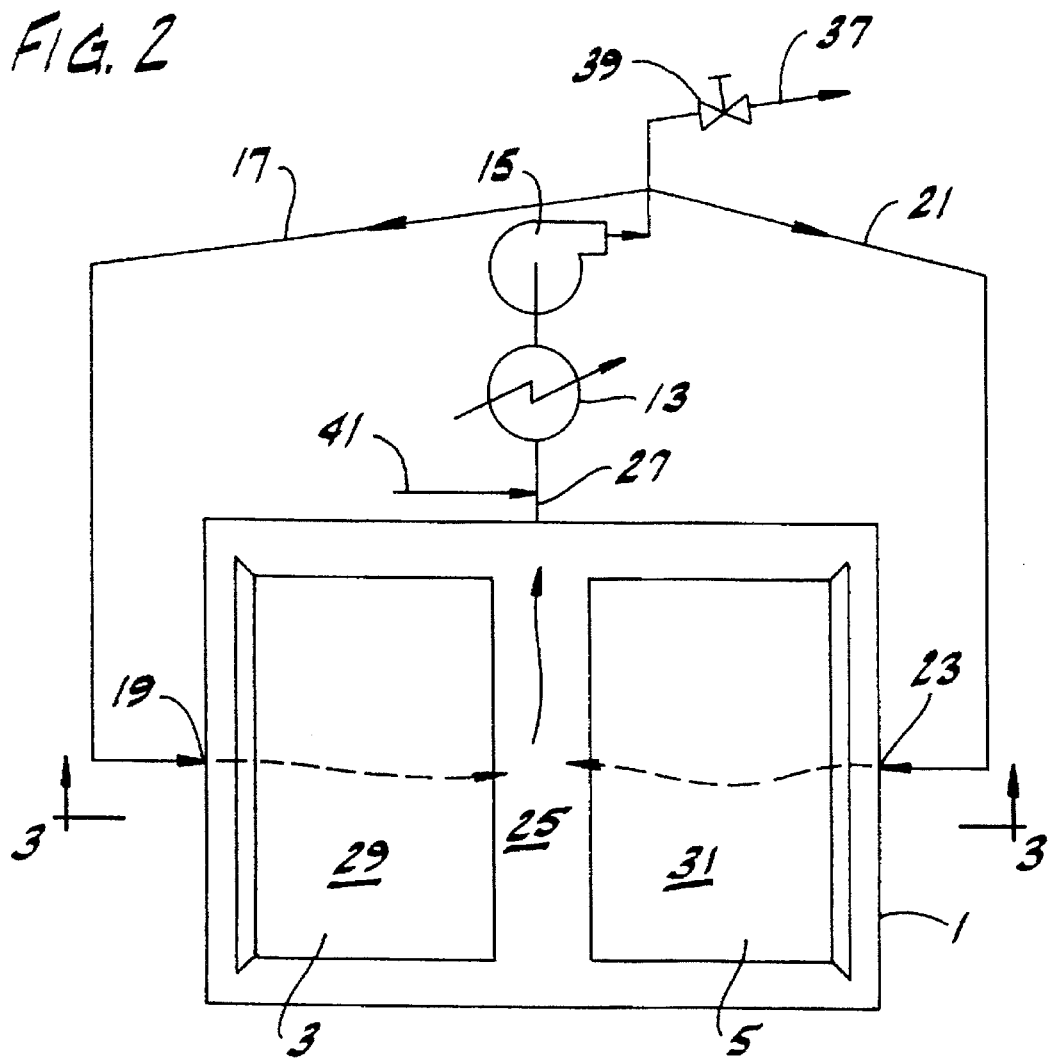
FIGS. 2 and 3 are schematic plan and sectional (along line 3—3) elevation diagrams, respectively, showing an apparatus useful in the removal of a pore modification agent from a tabletted catalyst precursor composition and recovery of the pore modification agent for reuse.
Figure 3:
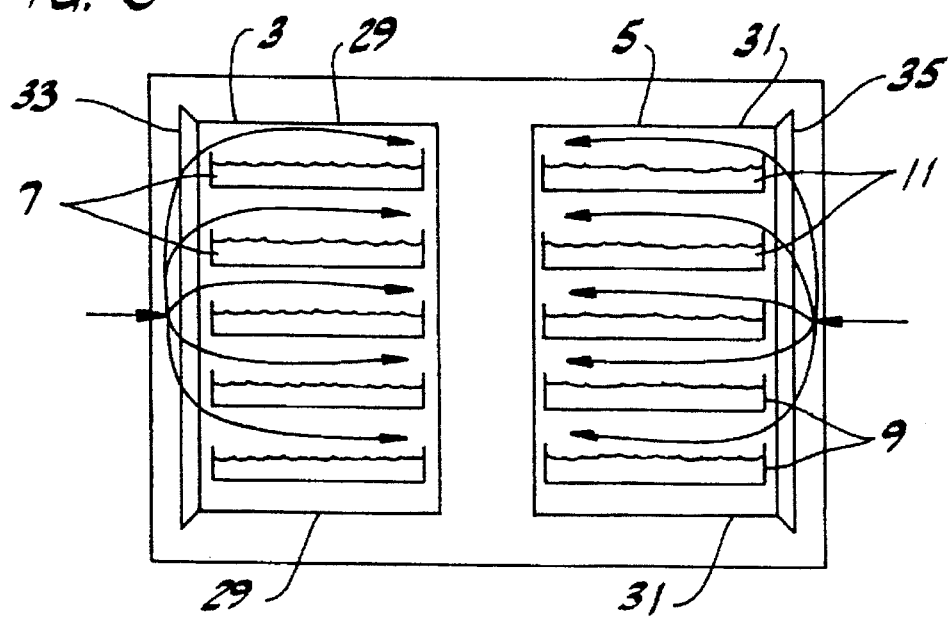

A system for removal of a pore builder is illustrated in FIGS. 2 and 3. In the apparatus shown, an oven 1 contains a pair of racks 3 and 5, each rack holding a plurality of trays 7, 9, and each tray in turn containing a relatively thin layer of shaped porous bodies 11 comprising the catalyst precursor composition containing the pore builder within their pores. Stripping air is circulated through oven 1 and an indirect heat exchanger 13 by means of a blower 15. Air exiting blower 15 is divided between a gas duct 17, which communicates with an air inlet 19 on one side of oven 1, and a 9as duct 21, which communicates with an inlet 23 on the other side of the oven opposite inlet 19. Rack 3 is located on the side of the oven adjacent inlet 19, rack 5 is located adjacent inlet 23, and a space between the racks constitutes a plenum 25 for collection of air circulated over the trays for return to the blower via a gas exit 27 of the oven and heat exchanger 13.

Each rack 3, 5 is open on the sides thereof facing the walls of the oven in which the stripping gas inlets 19 and 21 are located, but is covered with sheet metal walls 29, 31 on the top bottom, and the sides facing the other two walls of the oven. Thus, an enclosed "tunnel" is formed having one side open for inflow of stripping air and an opposite side open for exit of air containing pore builder stripped from the shaped catalyst bodies. On the inlet ("upwind") side of each rack, the sheet metal walls are extended beyond the edge of the rack and flared outwardly to form a louver 33, 35 to capture as much air as possible coming from the oven recirculating blower and direct it into the "tunnel" formed by walls 29, 31, thus providing the most desirable air flow over the catalyst precursor shaped bodies on the trays in the rack. Though not indicated in the drawing, each rack may contain two vertical arrays of trays, one adjacent the upwind and the other adjacent the downwind openings in the "tunnel."

In accordance with the process of the invention, air or other stripping or purge gas is passed over trays 7, 9 of shaped porous bodies for removal of vaporized pore builder from the shaped bodies. The stripping air is heated by indirect heat transfer in heat exchanger 13, the heat of vaporization of the pore builder being provided by direct heat transfer from the stripping air. The stripping gas flows over the trays at a velocity in the range noted above. In a preferred embodiment, as illustrated, the gas flows both over and under a relatively thin, e.g., 1" thick layer of precursor bodies. The pressure of the stripping gas and temperature of the shaped bodies falls within the ranges outlined above. During the concluding phase of the pore builder removal cycle, oxygen in the stripping gas may participate in controlled catalytic oxidation of residual builder while preventing abstraction of labile oxygens and reduction of vanadium.

As noted above, air is preferably used. To conserve energy the air is recirculated by means of a blower 15. A purge stream is discharged through line 37 and valve 39, while makeup air is drawn in through line 41. If desired, the purge may be regulated on a programmed basis at a rate proportional to the rate of vaporization/oxidation of pore builder, but is conveniently set at a fixed rate which preserves a substantial driving force for mass transfer during periods in which the rate of pore builder removal is at a maximum. The purge stream is conveyed to a combustion chamber where it is burned at high temperature to produce an innocuous exhaust gas comprising water vapor and carbon dioxide.

After removal of the pore builder, the shaped catalyst body is subjected to calcination or other heat treatment to convert the catalyst precursor composition to active catalyst. Preferably, the transformation to active catalyst is carried out in the manner described in copending and coassigned application Ser. No. 07/722,070, Attorneys' Docket No. 24-21 (7928), which is expressly incorporated herein by reference. This application describes catalysts having a composition represented by the formula $$(VO)_2(M)_m P_2 O_7 \bullet b(P_{2/c}O)$$ 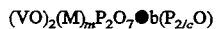

wherein M is at least one promoter element selected from among elements of Groups IA, IB, IIA, IIB, IIIA, IIIB, IVA, IVB, VA, VB, VIA, VIB, and VIIIA of the Periodic Table of the Elements, and mixtures thereof, m is a number from zero (0) to about 0.2, b is a number taken to provide a P/V atom ratio from about 1.0 to about 1.3, and c is a number representing the oxidation number of phosphorus and has a value of 5. The oxidation state of the vanadium is between about 4.0 and about 4.5, preferably between about 4.06 and about 4.30. The activated catalyst has a B.E.T. surface area of at least about 15 $m^2/g$, preferably at least about 20 $m^2/g$. By incorporating a substantial fraction of macropores, the activated catalyst provides avenues for access of reactant gases to the extensive active surface contained in what is also a high concentration of fine pores, and egress of product gases from the pores.

Although catalysts, as represented by the above formula, are indicated as having a phosphorus-to-vanadium (phosphorus/vanadium or P/V) atom ratio of from about 1.0 to about 1.3, preferably from about 1.0 to about 1.2, most preferably from about 1.05 to about 1.15, the actual P/V atom ratio may range from a value as low as about 0.9 up to the stated value of about 1.3. The total atom ratio of promoter element-to-vanadium (promoter element/vanadium or M/V), when a promoter element is present as a component of the catalyst, advantageously is in the range from about 0.0001 to about 0.2, preferably from about 0.0005 to about 0.1, most preferably from about 0.001 to about 0.05. These catalysts exhibit enhanced catalyst activity and excellent selectivities to and yields of maleic anhydride when compared to catalysts transformed from catalyst precursors via conventional procedures. Further enhancement of activity is provided by the use of a pore modification agent to produce high fractions of macropores as described above.

Catalyst precursors suitable for use in the process of the instant invention are those known in the art and in general are materials capable of being transformed in accordance with the process of the invention into active catalysts which are capable of catalyzing the vapor phase partial oxidation of non-aromatic hydrocarbons to maleic anhydride under oxidation conditions. Such catalyst precursors are represented by the formula $$VO(M)_m HPO_4 \bullet aH_2O \bullet b(P_{2/c}O) \bullet n(\text{organics})$$ 

wherein M, m, b, and c are as defined above, a is a number of at least about 0.5, and n is a number taken to represent the weight percent of intercalated or occluded organics component. The catalyst precursor may be prepared, for example, in an organic reaction medium such as primary and secondary alcohols-methanol, ethanol, 1-propanol; 2-propanol, 2-methyl-1-propanol (isobutyl alcohol), 3-methyl-2-butanol, 2,2-dimethyl-1-propanol, 1,2-ethanediol (ethylene glycol), for example. Intercalated or occluded organic materials (organics), as represented by the term "n(organics)" in the formula for the catalyst precursors, may represent up to 40% by weight, or higher, typically from about 2% by weight to about 25% by weight, of the catalyst precursor composition, depending upon the conditions (temperature and time) under which the catalyst precursor is dried. For example, if the catalyst precursor is dried at about 150° C. for about 8 hours, the intercalated organic materials typically represent about 25% by weight, while drying at about 250° C. for about 4 hours typically results in a catalyst precursor having about 2% by weight intercalated organic materials. In general, the preparation of the catalyst precursors in an organic reaction medium is preferred over preparations carried out in an aqueous medium. Most preferred among suitable organic reaction media are the previously noted primary and secondary alcohols, with isobutyl alcohol being most preferred.

Specific, albeit nonlimiting, examples of suitable catalyst precursor materials are those described in U.S. Pat. Nos. 4,632,916; 4,632,915; 4,567,158; 4,333,853; 4,315,864; 4,328,162; 4,251,390; 4,187,235; 3,864,280; and European Patent Application No. 98,039—it being understood however, that the same are not to be construed as limiting but instead are for purposes of illustration and guidance in the practice of the process of the instant invention. These references are herein incorporated by reference. Among such catalyst precursor materials, nonlimiting examples of those preferred for use in the process of the instant invention are those described in U.S. Pat. No. 4,632,915 and U.S. Pat. No. 4,567,158.

In the process of the invention, a particulate catalyst precursor material is mixed with a pore modification agent to produce a modified catalyst precursor composition which is formed into a predetermined shape under compression. As described above, the shaped body into which the precursor composition is formed has a volume of at least about 0.02 cc, more preferably at least about 0.03 cc, and most preferably, at least about 0.05 cc. The catalyst precursor composition contained in this shaped body is transformed into an active catalyst by a series of steps conveniently referred to as calcination. This transformation, which is critical for the preparation of superior catalysts, is accomplished in three stages. For convenience, these may be referred to as (1) initial heat-up stage, (2) rapid heat-up stage, and (3) maintenance/finishing stage. Removal of the pore builder as described above may be carried out either prior to or as part of the initial heat-up stage of the calcination.

In the initial heat-up stage, the catalyst precursor is heated in an atmosphere selected from among air, steam, inert gas, and mixtures thereof, at any convenient heat-up rate to a temperature not to exceed the phase transformation initiation temperature which is about 300° C. In general, suitable temperatures for the initial heat-up stage range from about 200° to about 300° C. with a temperature from about 250° to about 275° C. being preferred.

If removal of pore builder occurs primarily during this initial heat-up stage, this step should be carried out under the conditions outlined above. If the pore builder has been substantially removed prior to the initial heat-up stage of the transformation to active catalyst, it may still be desirable to program the introduction of oxygen-containing gas during the heat-up in order to avoid the possible development of an excessive exotherm which might prematurely dehydrate the precursor or otherwise adversely affect the activated catalyst. The criteria for exothermic temperature excursions are essentially the same as for the pore builder removal stage, as described hereinabove.

After the desired temperature has been achieved in the initial heat-up stage, the initially selected atmosphere (in the event it does not contain molecular oxygen and steam and/or has a different composition than that which is desired for the rapid heat-up stage) is replaced by a molecular oxygen/steam-containing atmosphere, while maintaining the catalyst precursor at the temperature achieved in the initial heat-up stage. Such atmosphere optionally may contain an inert gas and, as such, may be conveniently represented by the formula

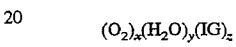

wherein IG is an inert gas and x, y, and z represent mol % (or volume %) of the $O_2$, $H_2O$, and IG components, respectively, in the molecular oxygen/steam-containing atmosphere, with x having a value greater than zero (0) mol %, but less than 100 mol %, y having a value greater than zero (0) mol %, but less than 100 mol %, and z having a value representing the balance of the molecular oxygen/steam-containing atmosphere. At least during the critical heating period, it is preferably at least about 5% by volume. A critical feature of the instant invention is that such atmosphere must contain at least a portion of molecular oxygen and water (as steam). The presence of the inert gas in such atmosphere, as indicated by the formula, is optional. Nonlimiting examples of suitable inert gases suitable for use in the molecular oxygen/steam-containing atmosphere include (molecular) nitrogen, helium, argon, and the like, with nitrogen generally being preferred for practical reasons.

Once the molecular oxygen/steam-containing atmosphere is provided, the catalyst precursor is subjected to the rapid heat-up stage of the calcination. In the rapid heat-up stage, the initial heat-up stage temperature of the catalyst is increased at a rate of from about 2° C. per minute (° C./min) to about 12° C./min, preferably from about 4° C./min to about 8° C./min, to a value effective to eliminate or remove the water of hydration from the catalyst precursor. In general, a temperature of from about 340° C. to about 450° C., usually at least about 375° C. to about 425° C. is suitable. Because of the importance of controlling the rate of increase during this temperature ramps it is essential that residual pore builder have been removed to the extent that it does not result in the generation of an exotherm at temperatures within the range of the ramp heating that would cause the rate of increase to significantly exceed about 12° C.

Because of the apparent presence of residual pore builder, or carbon resulting from coking of the pore builder during the pore builder removal step, it is important to control the heatup rate of the precursor bodies themselves within the aforesaid 2° to 12° C. range. To keep the rate of temperature increase within such range, the oven in which the calcination takes place is preferably heated at a rate no higher than about 3° C., more preferably not more than about 2° C. As noted above, a heatup rate approaching 12° C. per minute may result in a substantial exotherm. Where stearic acid is used as the pore builder, the optimal heatup rate is about 1.8° C. per minute. The acceptable level of residual pore builder remaining after the pore builder removal step may be defined with reference to transformation of the precursor to active catalyst at a standard or reference heating rate of 1.8° C. between 300° and 400° C. A maximum acceptable level of residual pore builder is that concentration which does not result in an exotherm that adversely alters or affects the VPO structure when the shaped bodies are heated for activation in the presence of air, steam or nitrogen under such reference conditions.

Following the rapid heat-up stage, the catalyst precursor is subjected to the maintenance/finishing stage of calcination. In the maintenance/finishing stage, the temperature, while maintaining the molecular oxygen/steam-containing atmosphere, is adjusted to a value greater than 350° C., but less than 550° C., preferably from about 375° C. to about 450° C., most preferably from about 400° C. to about 425° C. The adjusted temperature is then maintained, first in the molecular oxygen/steam-containing atmosphere for a time effective to provide a vanadium oxidation state of from about +4.06 to about +4.3 or simply from about 4.06 to about 4.3, and thereafter in a nonoxidizing, steam-containing atmosphere for a time effective to complete the catalyst precursor-to-active catalyst transformation to yield the active catalyst. In a manner similar to the molecular oxygen/steam-containing atmosphere, the nonoxidizing, steam-containing atmosphere also optionally may contain an inert gas, with nitrogen generally being the preferred inert gas for practical reasons.

The nonoxidizing, steam-containing atmosphere need not necessarily be completely free of molecular oxygen. However, such atmosphere preferably is substantially free of molecular oxygen. Accordingly, molecular oxygen may be present in an amount which is not effective to cause further oxidation of the vanadium beyond the desired oxidation state of about +4.06 to about +4.3. In general, molecular oxygen may be present in amounts which do not exceed about 0.5 mol % of the nonoxidizing, steam-containing atmosphere.

It will be apparent to those skilled in the art that the period of time during which the adjusted temperature is maintained in the molecular oxygen/steam-containing atmosphere in order to provide the desired vanadium oxidation state of from about +4.06 to about +4.3 will depend to some extent upon the vanadium oxidation state achieved during the rapid heat-up stage, which, in turn, will depend to some extent upon the period of time during which the catalyst precursor material is exposed to the molecular oxygen/steam-containing atmosphere at the stated rapid heat-up stage temperatures. In general, a period of time of from about 0.25 hour to about 4 hours is suitable, with a period of time of from about 1 hour to about 2 hours being preferred.

A suitable period of time during which the adjusted temperature is maintained in the nonoxidizing, steam-containing atmosphere is at least 1 hour, although longer periods of time up to 24 hours, or longer, may be employed, if desired, with a period of time of from about 3 hours to about 10 hours being preferred, and a period of about 6 hours being most preferred.

Figure 13:
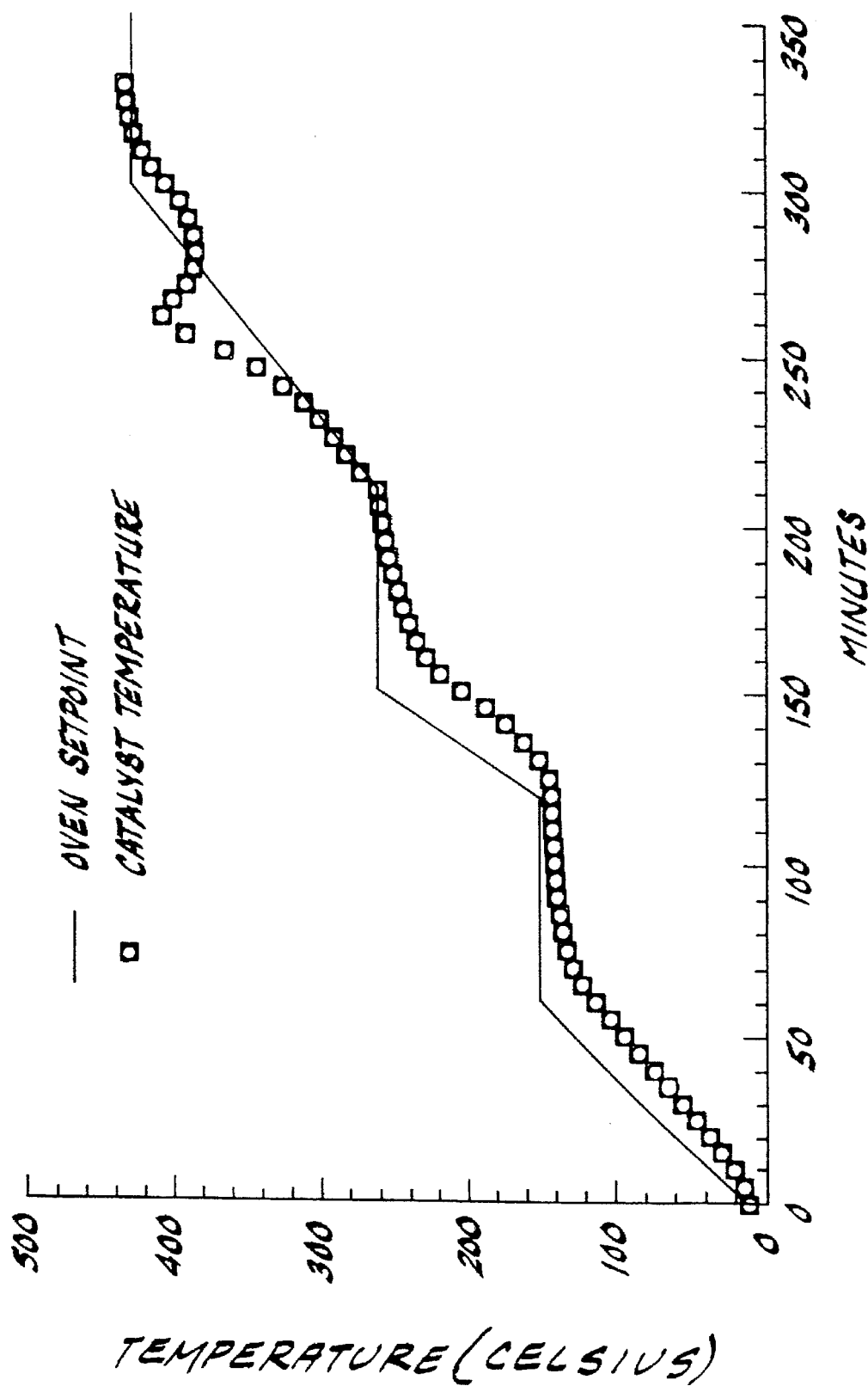
FIG. 13 is a plot of catalyst temperature and oven temperature vs. time during the preparation of an activated catalyst in accordance with the process of the present invention.

FIG. 13 illustrates typical profiles of both catalyst body temperature and oven temperature for the catalyst activation steps of the process of the invention. It may be noted that the circulating gas serves as a heat source in supplying the heat of vaporization during the pore builder removal step, but functions as a heat sink during the activation step when residual pore builder is oxidized. The circulating gas may also serve as a heat sink whenever a modest exotherm is incurred in removal of pore builder, for example, as illustrated in FIG. 5.

In accordance with the invention, it has been discovered that both the removal of pore builder and the transformation of catalyst precursor bodies to active catalyst bodies can be conducted in the same oven, without removal of the catalyst bodies from the oven between the end point of the pore builder removal step and the beginning of the transformation step. As indicated above, the end point of the pore builder removal step is determined by the residual concentration of pore builder, and/or carbonaceous degradation products of the pore builder, which must be reduced to such a level that no excessive exotherm is experienced in the subsequent activation step. To assure against such an exotherm, it is necessary that at least 80% by weight of the pore builder originally present be removed from the precursor bodies by raising the terminal temperature of the precursor bodies at the end point to at least about 200° C., preferably in the range of 240° to 260° C. Advantageously, the precursor bodies are not cooled below about 100° C. in the period between the end point of the removal step and the beginning of the activation step. More preferably, the precursor bodies are not allowed to cool by more than 50° C. during that period. Using this preferred embodiment of the process of the invention, enhanced productivity is achieved by avoiding the steps of cooling the precursor bodies, transferring them from one oven to another, and reheating them in the first step of the activation process. Substantial energy savings are also realized.

Catalysts of the present invention have been demonstrated to afford enhanced yields in the range of 2–4% higher than otherwise comparable catalysts that have not been processed to provide the proportions of macropores described hereinabove. The catalysts of the invention are also superior to catalysts which contain a similar proportion of macropores, but have been prepared by burning a pore builder out of a catalyst precursor tablet or pellet under conditions which expose the catalyst body to a substantial exotherm. Careful removal of the pore builder under mild conditions avoids the deposit of carbon on the active surfaces of the catalyst pores or abstraction of labile oxygens and reduction of the vanadium oxidation state, and further avoids interference with the critical chemistry by which the precursor is transformed to high surface area active catalyst under the controlled heating conditions described above.

FIGS. 8–12 are photomicrographs showing the external surface of a catalyst tablet of the invention. Distributed over the surface of this tablet are exit holes through which the pore builder has escaped during the process of its removal. By removal of the pore builder under mild conditions, a distribution is obtained in which the exit holes greater than about 2 microns in diameter have a density of at least about 75/mm$^2$, more preferably at least about 100/mm$^2$ on the external surfaces of the catalyst bodies. These holes are in communication with the interior of the body and further facilitate the ingress of reactant gases and egress of product gases.

The following examples illustrate the invention.

EXAMPLE 1

VPO catalyst precursor was prepared by reaction of vanadium oxide and phosphoric acid in an isobutyl alcohol medium as described in U.S. Pat. No. 5,275,996. The precipitated precursor was separated from the alcohol medium and dried in a roaster. Dry precursor powder (1500 pounds) containing up to 25% precursor powder dust recycled from downstream slugging and tableting operations was blended in a cone blender with graphite (4% by weight based on the final weight of the blend) and stearic acid (10% by weight based on the final weight of the blend) having an average particle diameter of about 43 μM. Since the recycle dust contained graphite and stearic acid in these proportions, fresh graphite was charged in a proportion of 4 wt % based on the total weight of fresh materials, and fresh stearic acid was charged in a proportion of 10 wt % based on the total weight of fresh materials. The fresh catalyst precursor, recycle dust, graphite and stearic acid components of the blender charge were weighed in drums and the transferred pneumatically to the cone blender. Once the charge was complete, the vessel was rotated end over end for approximately one hour to provide adequate mixing of the ingredients. Thereafter, the blended powder was transferred into feed hoppers that held approximately 1000 pounds each. The blend was transferred from these hoppers to the tableting operation.

The powder blend was prepared for tableting by preliminary slugging and granulating. The powder was first transferred by a screw conveyor to a feed charger ("feed frame") from which the powder was charged to a slugging press. Slug dies were rotated under the feed frame and filled by gravity flow of powder from the feed frame. Each die comprised a cylinder having piston-like punch in the bottom thereof for removal of the slug after compression. As the dies rotated away from the feed frame, the amount of material in each die was adjusted as necessary by raising the height of the lower punch slightly to cause excess powder to overflow the die. An upper punch was then pressed into the die to compress the powder in each die into a cylinder of approximately 0.25 in. in height and 0.75 in. in diameter. These slugs had a density of approximately 1.40 to 1.50 g/cc. Higher densities were avoided because compression to higher densities may cause expression of liquid fatty acid from certain grades of stearic acid, resulting in a change in the size and number of stearic particles.

The slugs were removed from the dies onto a conveyor on which they were transferred to a Jacobson mill. In the Jacobson mill the slugs were granulated via mechanical action of knives and exited the mill through an associated retaining screen. The particle size of the granules produced may be varied by varying the rotational speed of the mill. In granulating the slugs of this example, the mill was run at a speed of 1200 to 1500 rpm, and a retaining screen having ³⁄₃₂" holes was used.

Tablets were produced from the granulated slugs using a tableting press generally similar to the slugging press. Cylindrical tablets produced on the tableting press had a diameter of about 0.25", a length of 0.210±0.002 in., and a weight of 0.174 to 0.180 g. The tablets were collected in drum for transfer to the pore builder removal process, sometimes referred to hereinafter as "dewaxing."

Dewaxing was carried using apparatus of the type illustrated in FIGS. 2 and 3. Weighed portions of precursor tablets (13 pounds each) were placed into trays, each tray having a length of 29" and a width of 24". The bed of tablets thus produced in the trays had a height of about 1" These trays were placed in the oven on racks having vertically spaced supports slots to hold 19 vertically arrayed trays with a gap of about 1.5" between trays; and heated air was circulated over the trays for stripping of the stearic acid pore builder from the precursor. The racks were arranged to hold two parallel arrays (stacks) of vertically spaced trays, one stack adjacent the air inlet ("upwind") side of the rack, the other stack adjacent the air outlet ("downwind") side. In the vertical array on the inlet side, a tray was placed on each support slot, 19 trays in all. On the outlet side, trays were placed in every other slot, a total of 9, with a gap of 4" between trays. This arrangement provided the most advantageous pressure drop balance inside the dewax oven and, thus, the optimal air flow around the trays.

As illustrated in FIGS. 2 and 3, two racks of trays were placed in oven 1. The portion of the oven chamber accommodating each rack was approximately 5'×5'×5'. The racks were oriented with their exit sides adjacent each other and their inlet sides at opposite ends of the oven. By operation of a blower, air was circulated through the oven from both ends, flowing across the trays on the racks in the "tunnels," into a central plenum chamber at the common exit location of the racks and back through a heat exchanger to the suction of the blower. Total air flow was 9000 scfm, 4500 scfm across each rack. Linear flow velocity was about 100 to 150 ft/min. at ambient conditions across each tray. Air containing vaporized pore builder was purged from the circulating air stream at a rate of 1000 scfm, and this was balanced by flow of 1000 scfm fresh air into the loop. The circulating air was heated by transfer of heat from hot air in the indirect heat exchanger. Purge air was directed to a thermal oxidizer where the stearic acid vapor was burned to carbon dioxide and water vapor.

The temperature of the circulating air was slowly increased to heat the precursor tablets at a rate of 2° C. per minute to a temperature of 165° C. The temperature was held constant at 165° C. for 2 hours. Then, the precursor was heated from 165° C. to a first intermediate temperature of 199° C. at a rate of 2° C. per hour, and from 199° C. to a terminal temperature of 255° C. at a rate of 28° C. per hour. Thereafter, the precursor bodies were cooled to ambient temperature in about 1 hour. At temperatures above about 170° C., stearic acid is catalytically oxidized in the presence of the precursor composition, and a controlled burnoff takes place.

After precursor bodies had cooled, they were tested by differential scanning calorimetry for verification that the stearic acid had been essentially completely removed. Once that verification was established, the trays of precursor bodies were transferred to another oven for heat treatment to transform the precursor composition to active catalyst. The heat treatment oven was a single chamber unit similar in design to the dewax oven but adapted for direct heating of the atmosphere within the oven and capable of operation at much higher temperatures. As in the dewaxing oven, the trays of precursor bodies were placed on racks in which the trays were arrayed vertically with a gap of 1.5" between trays. The oven accommodated two racks of trays, with 38 trays on each rack. Unlike the racks used in the dewaxing oven, the racks used for transformation of the precursor were open to gas flow from all directions. Transformation of the precursor to active catalyst was carried out substantially in the manner described in U.S. Pat. No. 5,137,860. However, apparently due to small residual amounts of stearic acid in the pores of the precursor bodies, it was necessary to increase the temperature in the heat treatment oven at a rate somewhat slower than that found optimal for catalyst produced without a pore modification agent. Thus, the atmosphere within the oven was heated at a rate of only about 1.8° C. per minute, resulting in a 3° to 9° C. per minute increase in the temperature of the precursor bodies themselves.

After the activation step was completed, the pore size distribution of the catalyst was determined by the standard mercury intrusion porosimetry test. To provide a basis of comparison, the same porosimetry test was run on a catalyst which was prepared in substantially the same manner as the catalyst of this example, except that no pore modification agent was used in the preparation of the precursor shaped bodies. Results of the porosimetry tests are set forth in Tables 1 and 2. Plots of the pore size distributions of the two catalysts as measured by mercury intrusion are shown illustrated in FIG. 1.

TABLE 1

| Pore Diameter (microns) | Incremental Volume (ml/g) | Percent Incremental Volume | Percent Cummulative Volume |
|---|---|---|---|
| 300.0000 | 0.0000 | 0.00 | 0.00 |
| 179.2623 | 0.0005 | 0.19 | 0.19 |
| 143.5927 | 0.0001 | 0.04 | 0.23 |
| 119.7625 | 0.0002 | 0.08 | 0.31 |
| 86.1337 | 0.0004 | 0.16 | 0.47 |
| 67.2903 | 0.0004 | 0.16 | 0.62 |
| 51.6881 | −0.0001 | −0.04 | 0.58 |
| 40.4661 | 0.0003 | 0.12 | 0.70 |
| 31.3759 | 0.0003 | 0.12 | 0.82 |
| 24.5693 | 0.0001 | 0.04 | 0.85 |
| 19.1229 | 0.0001 | 0.04 | 0.89 |
| 14.9069 | 0.0004 | 0.16 | 1.05 |
| 12.3683 | 0.0001 | 0.04 | 1.09 |
| 9.0387 | 0.0004 | 0.16 | 1.24 |
| 7.0202 | 0.0007 | 0.27 | 1.52 |
| 6.0480 | 0.0002 | 0.08 | 1.59 |
| 4.2846 | 0.0005 | 0.19 | 1.79 |
| 3.3326 | 0.0007 | 0.27 | 2.06 |
| 2.5857 | 0.0006 | 0.23 | 2.29 |
| 2.0157 | 0.0012 | 0.47 | 2.76 |
| 1.5590 | 0.0015 | 0.58 | 3.34 |
| 1.2188 | 0.0028 | 1.09 | 4.43 |
| 0.9478 | 0.0030 | 1.17 | 5.59 |
| 0.7400 | 0.0039 | 1.52 | 7.11 |
| 0.5750 | 0.0053 | 2.06 | 9.17 |
| 0.4494 | 0.0065 | 2.53 | 11.69 |
| 0.3488 | 0.0060 | 2.33 | 14.02 |
| 0.2720 | 0.0065 | 2.53 | 16.55 |
| 0.2123 | 0.0064 | 2.49 | 19.04 |
| 0.1644 | 0.0062 | 2.41 | 21.45 |
| 0.1282 | 0.0112 | 4.35 | 25.80 |
| 0.1003 | 0.0200 | 7.77 | 33.57 |
| 0.0781 | 0.0392 | 15.23 | 48.80 |
| 0.0628 | 0.0397 | 15.42 | 64.22 |
| 0.0604 | 0.0012 | 0.47 | 64.69 |
| 0.0473 | 0.0365 | 14.18 | 78.87 |
| 0.0369 | 0.0177 | 6.88 | 85.74 |
| 0.0313 | 0.0049 | 1.90 | 87.65 |
| 0.0286 | 0.0029 | 1.13 | 88.77 |
| 0.0224 | 0.0121 | 4.70 | 93.47 |
| 0.0174 | 0.0042 | 1.63 | 95.10 |
| 0.0136 | 0.0037 | 1.44 | 96.54 |
| 0.0106 | 0.0016 | 0.62 | 97.16 |
| 0.0082 | 0.0018 | 0.70 | 97.86 |
| 0.0064 | 0.0014 | 0.54 | 98.41 |
| 0.0050 | 0.0012 | 0.47 | 98.87 |
| 0.0039 | 0.0014 | 0.54 | 99.42 |
| 0.0031 | 0.0015 | 0.58 | 100.00 |

TABLE 2

| Prior Art Pore Diameter (microns) | Prior Art Incremental Volume (ml/g) | Prior Art Percent Incremental Volume | Prior Art Percent Cummulative Volume |
|---|---|---|---|
| 393.6248 | 0.0000 | 0.00 | 0.00 |
| 268.7924 | 0.0017 | 0.75 | 0.75 |
| 131.8612 | 0.0002 | 0.09 | 0.84 |
| 103.0141 | 0.0010 | 0.44 | 1.28 |
| 76.7579 | 0.0002 | 0.09 | 1.37 |
| 59.5883 | 0.0002 | 0.09 | 1.45 |
| 46.1673 | 0.0001 | 0.04 | 1.50 |
| 35.8920 | 0.0007 | 0.31 | 1.81 |
| 27.9914 | 0.0002 | 0.09 | 1.89 |
| 21.8714 | 0.0001 | 0.04 | 1.94 |
| 17.0155 | 0.0002 | 0.09 | 2.03 |
| 13.6331 | 0.0003 | 0.13 | 2.16 |
| 10.7045 | 0.0001 | 0.04 | 2.20 |
| 8.0368 | 0.0002 | 0.09 | 2.29 |
| 6.5403 | 0.0003 | 0.13 | 2.42 |
| 5.0966 | 0.0004 | 0.18 | 2.60 |
| 3.7449 | 0.0001 | 0.04 | 2.64 |
| 2.9684 | 0.0000 | 0.00 | 2.64 |
| 2.3087 | 0.0001 | 0.04 | 2.69 |
| 1.7974 | 0.0001 | 0.04 | 2.73 |
| 1.3969 | 0.0002 | 0.09 | 2.82 |
| 1.0866 | 0.0001 | 0.04 | 2.86 |
| 0.8470 | 0.0002 | 0.09 | 2.95 |
| 0.6594 | 0.0001 | 0.04 | 2.99 |
| 0.5128 | 0.0001 | 0.04 | 3.04 |
| 0.3977 | 0.0001 | 0.04 | 3.08 |
| 0.3087 | 0.0007 | 0.31 | 3.39 |
| 0.2417 | 0.0010 | 0.44 | 3.83 |
| 0.1876 | 0.0031 | 1.37 | 5.20 |
| 0.1455 | 0.0083 | 3.65 | 8.85 |
| 0.1144 | 0.0228 | 10.04 | 18.89 |
| 0.0893 | 0.0401 | 17.66 | 36.55 |
| 0.0704 | 0.0299 | 13.17 | 49.71 |
| 0.0616 | 0.0019 | 0.84 | 50.55 |
| 0.0540 | 0.0291 | 12.81 | 63.36 |
| 0.0422 | 0.0179 | 7.88 | 71.25 |
| 0.0341 | 0.0068 | 2.99 | 74.24 |
| 0.0300 | 0.0040 | 1.76 | 76.00 |
| 0.0255 | 0.0151 | 6.65 | 82.65 |
| 0.0199 | 0.0087 | 3.83 | 86.48 |
| 0.0155 | 0.0084 | 3.70 | 90.18 |
| 0.0121 | 0.0054 | 2.38 | 92.56 |
| 0.0094 | 0.0047 | 2.07 | 94.63 |
| 0.0073 | 0.0037 | 1.63 | 96.26 |
| 0.0057 | 0.0031 | 1.37 | 97.62 |
| 0.0044 | 0.0027 | 1.19 | 98.81 |
| 0.0035 | 0.0027 | 1.19 | 100.00 |

EXAMPLES 2–9

A series of catalysts was prepared substantially in the manner described in Example 1. Set forth in Table 3 are the time and temperature conditions under which the pore builder was removed from the catalyst precursors of these Examples, and the ramp catalyst body heating rate during catalyst activation.

TABLE 3

| Batch | R.T. to Hold Temp. | Hold Temp. | Hold Period | Dewax Schedule After Hold Period | Activation Ramp Rate |
|---|---|---|---|---|---|
| 6[a] | 1 h | 165° C. | 2 h | 165° C.–199° C.; 17 h<br>199° C.–255° C.; 2 h | 1.8° C./h |
| 7[b] | 1 h | 165° C. | 2 h | 165° C.–199° C.; 17 h<br>199° C.–255° C.; 2 h | 1.8° C./h |
| 9[c] | 1 h | 165° C. | 2 h | 165° C.–199° C.; 17 h<br>199° C.–255° C.; 2 h | 1.8° C./h |
| 21[d] | 1 h | 165° C. | 2 h | 165° C.–199° C.; 17 h<br>199° C.–255° C.; 2 h | 1.8° C./h |
| 22[e] | 1 h | 165° C. | 2 h | 165° C.–199° C.; 17 h<br>199° C.–255° C.; 2 h | 1.8° C./h |
| 23[f] | 1 h | 165° C. | 2 h | 165° C.–199° C.; 17 h<br>199° C.–255° C.; 2 h | 1.8° C./h |
| 24[g] | 1 h | 165° C. | 2 h | 165° C.–199° C.; 17 h<br>199° C.–255° C.; 2 h | 1.8° C./h |
| 25[h] | 1 h | 165° C. | 2 h | 165° C.–199° C.; 17 h<br>199° C.–255° C.; 2 h | 1.8° C./h |

[a]Example 2
[b]Example 3
[c]Example 4
[d]Example 5
[e]Example 6
[f]Example 7
[g]Example 8
[h]Example 9

For each of the activated catalysts of these Examples, the pore volume distribution was determined by mercury porosimetry, the vanadium oxidation state was determined by chemical titration, and the surface area was determined by the B.E.T. method. The dimensions, % "broken pills" (B.P.(%)), wt % minus 10 mesh particles (% -10M), bulk density (B.D.) (g/cc), B.E.T. surface area ($m^2/g$), vanadium oxidation state, and phosphorus to vanadium ratios for the catalysts of these examples are set forth in Table 4. Results of the porosimetry tests are set forth in Tables 5 to 11.

TABLE 4

PROPERTIES OF ANST BATCHES

| Example | Batch Number | Crush (lbs.) | Weight (grams) | Length (inches) | B.P. (%) | -10 Mesh (%) | B.D. (g/cc) | S.A. ($m^2/g$) | VOX | P/V |
|---|---|---|---|---|---|---|---|---|---|---|
| 2 | 6 | 8.5 | 0.131 | 0.200 | 0.34 | 0.34 | 0.631 | 22 | 4.21 | 1.071 |
| 3 | 7 | 8.4 | 0.136 | 0.203 | 0.18 | 0.37 | 0.615 | 19 | 4.14 | 1.084 |
| 4 | 9 | 9.2 | 0.133 | 0.200 | 0.43 | 0.49 | 0.614 | 23 | 4.19 | 1.085 |
| 5 | 21 | 10.1 | 0.139 | 0.204 | 0.94 | 0.16 | 0.667 | 17 | 4.16 | 1.078 |
| 6 | 22 | 7.8 | 0.139 | 0.203 | 0.74 | 0.12 | 0.646 | 14 | 4.16 | 1.075 |
| 7 | 23 | 10.3 | 0.145 | 0.204 | 0.61 | 0.20 | 0.649 | 23 | 4.18 | 1.086 |
| 8 | 24 | 8.3 | 0.142 | 0.205 | 0.53 | 0.14 | 0.643 | 22 | 4.18 | 1.088 |
| 9 | 25 | 11.5 | 0.143 | 0.208 | 0.49 | 0.35 | 0.650 | 18 | 4.17 | 1.077 |
| Average | | 8.23 | 0.123 | 0.181 | 0.473 | 0.241 | 0.568 | 17.6 | 4.17 | 1.080 |
| Standard Deviation | | 3.117 | 0.044 | 0.064 | 0.267 | 0.146 | 0.202 | 6.849 | 0.020 | 0.006 |

TABLE 5

Excel DATA1.107 (Batch 6)

| PORE DIAMETER μm | Incremental Intrusion mL/g | Incremental Intrusion Percent | Cummulative Intrusion Percent | PORE DIAMETER μm | Incremental Intrusion mL/g | Incremental Intrusion Percent |
|---|---|---|---|---|---|---|
| 300 | 0 | 0.00 | 0.00 | | | |
| 179.2623 | 0.0005 | 0.19 | 0.19 | | | |
| 143.5927 | 1E-04 | 0.04 | 0.23 | | | |
| 119.7625 | 0.0002 | 0.08 | 0.31 | | | |
| 86.1337 | 0.0004 | 0.16 | 0.47 | | | |
| 67.2903 | 0.0004 | 0.16 | 0.62 | | | |
| 51.6881 | −0.0001 | −0.04 | 0.58 | | | |
| 40.4661 | 0.0003 | 0.12 | 0.70 | | | |
| 31.3759 | 0.0003 | 0.12 | 0.82 | | | |
| 24.5693 | 0.0001 | 0.04 | 0.85 | | | |
| 19.1229 | 1E-04 | 0.04 | 0.89 | | | |
| 14.9069 | 0.0004 | 0.16 | 1.05 | | | |
| 12.3683 | 1E-04 | 0.04 | 1.09 | | | |
| 9.0387 | 0.0004 | 0.16 | 1.24 | | | |
| 7.0202 | 0.0007 | 0.27 | 1.52 | | | |
| 6.048 | 0.0002 | 0.08 | 1.59 | | | |
| 4.2846 | 0.0005 | 0.19 | 1.79 | | | |
| 3.3326 | 0.0007 | 0.27 | 2.06 | 3.3326 | 0.0007 | 0.27 |
| 2.5857 | 0.0006 | 0.23 | 2.29 | 2.5857 | 0.0006 | 0.23 |
| 2.0157 | 0.0012 | 0.47 | 2.76 | 2.0157 | 0.0012 | 0.47 |
| 1.559 | 0.0015 | 0.58 | 3.34 | 1.559 | 0.0015 | 0.58 |
| 1.2188 | 0.0028 | 1.09 | 4.43 | 1.2188 | 0.0028 | 1.09 |
| 0.9478 | 0.003 | 1.17 | 5.59 | 0.9478 | 0.003 | 1.17 |
| 0.74 | 0.0039 | 1.52 | 7.11 | 0.74 | 0.0039 | 1.52 |
| 0.575 | 0.0053 | 2.06 | 9.17 | 0.575 | 0.0053 | 2.06 |
| 0.4494 | 0.0065 | 2.53 | 11.69 | 0.4494 | 0.0065 | 2.53 |
| 0.3488 | 0.006 | 2.33 | 14.02 | 0.3488 | 0.006 | 2.33 |
| 0.272 | 0.0065 | 2.53 | 16.55 | 0.272 | 0.0065 | 2.53 |
| 0.2123 | 0.0064 | 2.49 | 19.04 | 0.2123 | 0.0064 | 2.49 |
| 0.1644 | 0.0062 | 2.41 | 21.45 | 0.1644 | 0.0062 | 2.41 |
| 0.1282 | 0.0112 | 4.35 | 25.80 | 0.1282 | 0.0112 | 4.35 |
| 0.1003 | 0.02 | 7.77 | 33.57 | 0.1003 | 0.02 | 7.77 |
| 0.0781 | 0.0392 | 15.23 | 48.80 | total | 0.0818 | 31.78 |
| 0.0628 | 0.0397 | 15.42 | 64.22 | | | |
| 0.0604 | 0.0012 | 0.47 | 64.69 | double check | 31.78 | 31.78 |
| 0.0473 | 0.0365 | 14.18 | 78.87 | | | |
| 0.0369 | 0.0177 | 6.88 | 85.74 | answer is | 31.78 | |
| 0.0313 | 0.0049 | 1.90 | 87.65 | | | |
| 0.0286 | 0.0029 | 1.13 | 88.77 | | | |
| 0.0224 | 0.0121 | 4.70 | 93.47 | | | |
| 0.0174 | 0.0042 | 1.63 | 95.10 | | | |
| 0.0136 | 0.0037 | 1.44 | 96.54 | | | |
| 0.0106 | 0.0016 | 0.62 | 97.16 | | | |
| 0.0082 | 0.0018 | 0.70 | 97.86 | | | |
| 0.0064 | 0.0014 | 0.54 | 98.41 | | | |
| 0.005 | 0.0012 | 0.47 | 98.87 | | | |
| 0.0039 | 0.0014 | 0.54 | 99.42 | | | |
| 0.0031 | 0.0015 | 0.58 | 100.00 | | | |
| total | 0.2574 | 100.00 | | | | |

TABLE 6

Excel DATA1.110 (Batch 7)

| PORE DIAMETER μm | Incremental Intrusion mL/g | Incremental Intrusion Percent | Cummulative Intrusion Percent | PORE DIAMETER μm | Incremental Intrusion mL/g | Incremental Intrusion Percent |
|---|---|---|---|---|---|---|
| 300 | 0 | 0.00 | 0.00 | | | |
| 179.5482 | 0.0009 | 0.26 | 0.26 | | | |
| 143.7761 | 0.0008 | 0.23 | 0.50 | | | |
| 120.0178 | 0.0006 | 0.18 | 0.67 | | | |
| 85.8709 | 0.0006 | 0.18 | 0.85 | | | |
| 67.21 | 0.0001 | 0.03 | 0.88 | | | |
| 51.7832 | 0.0007 | 0.20 | 1.08 | | | |
| 40.3935 | 0.0003 | 0.09 | 1.17 | | | |
| 31.3584 | 0.0001 | 0.03 | 1.20 | | | |
| 24.6069 | 0 | 0.00 | 1.20 | | | |

TABLE 6-continued

Excel DATA1.110 (Batch 7)

| PORE DIAMETER μm | Incremental Intrusion mL/g | Incremental Intrusion Percent | Cummulative Intrusion Percent | PORE DIAMETER μm | Incremental Intrusion mL/g | Incremental Intrusion Percent |
|---|---|---|---|---|---|---|
| 19.1229 | 0.0005 | 0.15 | 1.35 | | | |
| 14.897 | 0.0002 | 0.06 | 1.41 | | | |
| 12.3643 | 0.0004 | 0.12 | 1.52 | | | |
| 9.0423 | 0.0003 | 0.09 | 1.61 | | | |
| 7.0207 | 0.0005 | 0.15 | 1.76 | | | |
| 6.0483 | 0.0008 | 0.23 | 1.99 | | | |
| 4.2406 | 0.0006 | 0.18 | 2.17 | | | |
| 3.3129 | 0.0012 | 0.35 | 2.52 | 3.3129 | 0.0012 | 0.35 |
| 2.5791 | 0.0023 | 0.67 | 3.19 | 2.5791 | 0.0023 | 0.67 |
| 2.0118 | 0.0024 | 0.70 | 3.89 | 2.0118 | 0.0024 | 0.70 |
| 1.5654 | 0.0052 | 1.52 | 5.42 | 1.5654 | 0.0052 | 1.52 |
| 1.2172 | 0.0063 | 1.84 | 7.26 | 1.2172 | 0.0063 | 1.84 |
| 0.9498 | 0.0092 | 2.69 | 9.95 | 0.9498 | 0.0092 | 2.69 |
| 0.7408 | 0.0107 | 3.13 | 13.09 | 0.7408 | 0.0107 | 3.13 |
| 0.5725 | 0.0113 | 3.31 | 16.39 | 0.5725 | 0.0113 | 3.31 |
| 0.4494 | 0.0098 | 2.87 | 19.26 | 0.4494 | 0.0098 | 2.87 |
| 0.3502 | 0.0075 | 2.20 | 21.46 | 0.3502 | 0.0075 | 2.20 |
| 0.2726 | 0.0067 | 1.96 | 23.42 | 0.2726 | 0.0067 | 1.96 |
| 0.2117 | 0.0062 | 1.81 | 25.23 | 0.2117 | 0.0062 | 1.81 |
| 0.1646 | 0.0094 | 2.75 | 27.99 | 0.1646 | 0.0094 | 2.75 |
| 0.1286 | 0.0184 | 5.39 | 33.37 | 0.1286 | 0.0184 | 5.39 |
| 0.1003 | 0.0333 | 9.75 | 43.12 | 0.1003 | 0.0333 | 9.75 |
| 0.0779 | 0.0436 | 12.76 | 55.88 | total | 0.1399 | 40.95 |
| 0.0627 | 0.0339 | 9.92 | 65.81 | | | |
| 0.0605 | 0.0015 | 0.44 | 66.25 | double check | 40.95 | 40.95 |
| 0.0474 | 0.0345 | 10.10 | 76.35 | | | |
| 0.0369 | 0.0182 | 5.33 | 81.67 | answer is | 40.95 | |
| 0.0314 | 0.0074 | 2.17 | 83.84 | | | |
| 0.0287 | 0.004 | 1.17 | 85.01 | | | |
| 0.0224 | 0.0146 | 4.27 | 89.29 | | | |
| 0.0174 | 0.0069 | 2.02 | 91.31 | | | |
| 0.0136 | 0.0064 | 1.87 | 93.18 | | | |
| 0.0106 | 0.004 | 1.17 | 94.35 | | | |
| 0.0082 | 0.0036 | 1.05 | 95.40 | | | |
| 0.0064 | 0.0041 | 1.20 | 96.60 | | | |
| 0.005 | 0.0036 | 1.05 | 97.66 | | | |
| 0.0039 | 0.004 | 1.17 | 98.83 | | | |
| 0.0031 | 0.004 | 1.17 | 100.00 | | | |
| total | 0.3416 | 100.00 | | | | |

TABLE 7

Excel DATA1.112 (Batch 9)

| PORE DIAMETER μm | Incremental Intrusion mL/g | Incremental Intrusion Percent | Cummulative Intrusion Percent | PORE DIAMETER μm | Incremental Intrusion mL/g | Incremental Intrusion Percent |
|---|---|---|---|---|---|---|
| 300 | 0 | 0.00 | 0.00 | | | |
| 178.1277 | 0.0011 | 0.33 | 0.33 | | | |
| 142.6828 | 0.0009 | 0.27 | 0.60 | | | |
| 119.3815 | 0.0004 | 0.12 | 0.72 | | | |
| 86.1996 | 0.0003 | 0.09 | 0.81 | | | |
| 66.9303 | 0.0002 | 0.06 | 0.87 | | | |
| 51.8787 | 0.0005 | 0.15 | 1.02 | | | |
| 40.2779 | 0.0003 | 0.09 | 1.11 | | | |
| 31.3497 | 0.0003 | 0.09 | 1.20 | | | |
| 24.5962 | 0.0003 | 0.09 | 1.29 | | | |
| 19.1197 | 0.0007 | 0.21 | 1.50 | | | |
| 14.895 | 0.0002 | 0.06 | 1.56 | | | |
| 12.3548 | 0.0004 | 0.12 | 1.69 | | | |
| 9.0336 | 0.0003 | 0.09 | 1.78 | | | |
| 7.036 | 0.0004 | 0.12 | 1.90 | | | |
| 6.0353 | 0.0006 | 0.18 | 2.08 | | | |
| 4.2653 | 0.001 | 0.30 | 2.38 | | | |
| 3.3259 | 0.001 | 0.30 | 2.68 | 3.3259 | 0.001 | 0.30 |
| 2.5889 | 0.0029 | 0.87 | 3.55 | 2.5889 | 0.0029 | 0.87 |
| 2.0173 | 0.0041 | 1.23 | 4.78 | 2.0173 | 0.0041 | 1.23 |
| 1.5655 | 0.0071 | 2.14 | 6.92 | 1.5655 | 0.0071 | 2.14 |

TABLE 7-continued

Excel DATA1.112 (Batch 9)

| PORE DIAMETER μm | Incremental Intrusion mL/g | Incremental Intrusion Percent | Cummulative Intrusion Percent | PORE DIAMETER μm | Incremental Intrusion mL/g | Incremental Intrusion Percent |
|---|---|---|---|---|---|---|
| 1.2166 | 0.0092 | 2.77 | 9.69 | 1.2166 | 0.0092 | 2.77 |
| 0.9482 | 0.0106 | 3.19 | 12.88 | 0.9482 | 0.0106 | 3.19 |
| 0.7418 | 0.0116 | 3.49 | 16.37 | 0.7418 | 0.0116 | 3.49 |
| 0.5762 | 0.0104 | 3.13 | 19.50 | 0.5762 | 0.0104 | 3.13 |
| 0.4495 | 0.0084 | 2.53 | 22.03 | 0.4495 | 0.0084 | 2.53 |
| 0.3502 | 0.0066 | 1.99 | 24.01 | 0.3502 | 0.0066 | 1.99 |
| 0.2723 | 0.0056 | 1.69 | 25.70 | 0.2723 | 0.0056 | 1.69 |
| 0.2124 | 0.0058 | 1.75 | 27.45 | 0.2124 | 0.0058 | 1.75 |
| 0.1636 | 0.0079 | 2.38 | 29.82 | 0.1636 | 0.0079 | 2.38 |
| 0.1287 | 0.0151 | 4.54 | 34.37 | 0.1287 | 0.0151 | 4.54 |
| 0.1001 | 0.0367 | 11.04 | 45.41 | 0.1001 | 0.0367 | 11.04 |
| 0.0781 | 0.0401 | 12.07 | 57.48 | total | 0.143 | 43.03 |
| 0.0626 | 0.0314 | 9.45 | 66.93 | | | |
| 0.0605 | 0.0005 | 0.15 | 67.08 | double check | 43.03 | 43.03 |
| 0.0474 | 0.029 | 8.73 | 75.80 | | | |
| 0.0369 | 0.0178 | 5.36 | 81.16 | answer is | 43.03 | |
| 0.0313 | 0.0053 | 1.59 | 82.76 | | | |
| 0.0287 | 0.004 | 1.20 | 83.96 | | | |
| 0.0224 | 0.0148 | 4.45 | 88.41 | | | |
| 0.0174 | 0.008 | 2.41 | 90.82 | | | |
| 0.0136 | 0.0071 | 2.14 | 92.96 | | | |
| 0.0106 | 0.0046 | 1.38 | 94.34 | | | |
| 0.0082 | 0.0033 | 0.99 | 95.34 | | | |
| 0.0064 | 0.0045 | 1.35 | 96.69 | | | |
| 0.005 | 0.0026 | 0.78 | 97.47 | | | |
| 0.0039 | 0.0039 | 1.17 | 98.65 | | | |
| 0.0031 | 0.0045 | 1.35 | 100.00 | | | |
| total | 0.3323 | 100.00 | | | | |

TABLE 8

Excel DATA1.123 (Batch 21)

| PORE DIAMETER μm | Incremental Intrusion mL/g | Incremental Intrusion Percent | Cummulative Intrusion Percent | PORE DIAMETER μm | Incremental Intrusion mL/g | Incremental Intrusion Percent |
|---|---|---|---|---|---|---|
| 300 | 0 | 0.00 | 0.00 | | | |
| 177.5658 | 0.0007 | 0.27 | 0.27 | | | |
| 143.96 | 0.0003 | 0.11 | 0.38 | | | |
| 120.1459 | 0.0002 | 0.08 | 0.46 | | | |
| 85.6097 | 0.0008 | 0.31 | 0.77 | | | |
| 66.9303 | 0.0003 | 0.11 | 0.88 | | | |
| 51.7832 | 0.0006 | 0.23 | 1.11 | | | |
| 40.408 | 0.0001 | 0.04 | 1.15 | | | |
| 31.3497 | 1E-04 | 0.04 | 1.19 | | | |
| 24.564 | 0.0005 | 0.19 | 1.38 | | | |
| 19.1294 | 0.0008 | 0.31 | 1.68 | | | |
| 14.8931 | 0.0003 | 0.11 | 1.80 | | | |
| 12.3683 | 0.0004 | 0.15 | 1.95 | | | |
| 9.0105 | 0.0006 | 0.23 | 2.18 | | | |
| 7.036 | 0.0009 | 0.34 | 2.53 | | | |
| 6.0363 | 0.001 | 0.38 | 2.91 | | | |
| 4.2586 | −0.0006 | −0.23 | 2.68 | | | |
| 3.3261 | 0.0017 | 0.65 | 3.33 | 3.3261 | 0.0017 | 0.65 |
| 2.5893 | 0.0034 | 1.30 | 4.63 | 2.5893 | 0.0034 | 1.30 |
| 2.0137 | 0.0045 | 1.72 | 6.35 | 2.0137 | 0.0045 | 1.72 |
| 1.5677 | 0.0046 | 1.76 | 8.11 | 1.5677 | 0.0046 | 1.76 |
| 1.2171 | 0.0053 | 2.03 | 10.14 | 1.2171 | 0.0053 | 2.03 |
| 0.9496 | 0.0069 | 2.64 | 12.78 | 0.9496 | 0.0069 | 2.64 |
| 0.7418 | 0.0084 | 3.21 | 16.00 | 0.7418 | 0.0084 | 3.21 |
| 0.5757 | 0.0082 | 3.14 | 19.14 | 0.5757 | 0.0082 | 3.14 |
| 0.4477 | 0.0074 | 2.83 | 21.97 | 0.4477 | 0.0074 | 2.83 |
| 0.3499 | 0.0054 | 2.07 | 24.03 | 0.3499 | 0.0054 | 2.07 |
| 0.2706 | 0.0048 | 1.84 | 25.87 | 0.2706 | 0.0048 | 1.84 |
| 0.2121 | 0.0044 | 1.68 | 27.55 | 0.2121 | 0.0044 | 1.68 |
| 0.1632 | 0.0058 | 2.22 | 29.77 | 0.1632 | 0.0058 | 2.22 |
| 0.1282 | 0.0084 | 3.21 | 32.99 | 0.1282 | 0.0084 | 3.21 |
| 0.1003 | 0.0168 | 6.43 | 39.42 | 0.1003 | 0.0168 | 6.43 |

TABLE 8-continued

Excel DATA1.123 (Batch 21)

| PORE DIAMETER μm | Incremental Intrusion mL/g | Incremental Intrusion Percent | Cummulative Intrusion Percent | PORE DIAMETER μm | Incremental Intrusion mL/g | Incremental Intrusion Percent |
|---|---|---|---|---|---|---|
| 0.0781 | 0.0243 | 9.30 | 48.72 | total | 0.096 | 36.74 |
| 0.0628 | 0.0239 | 9.15 | 57.86 | | | |
| 0.0604 | 0.0006 | 0.23 | 58.09 | double check | 36.74 | 36.74 |
| 0.0474 | 0.0266 | 10.18 | 68.27 | | | |
| 0.0369 | 0.0209 | 8.00 | 76.27 | answer is | 36.74 | |
| 0.0313 | 0.0074 | 2.83 | 79.10 | | | |
| 0.0287 | 0.005 | 1.91 | 81.02 | | | |
| 0.0224 | 0.0165 | 6.31 | 87.33 | | | |
| 0.0174 | 0.0079 | 3.02 | 90.36 | | | |
| 0.0136 | 0.0075 | 2.87 | 93.23 | | | |
| 0.0106 | 0.0035 | 1.34 | 94.57 | | | |
| 0.0082 | 0.0037 | 1.42 | 95.98 | | | |
| 0.0064 | 0.0031 | 1.19 | 97.17 | | | |
| 0.005 | 0.0021 | 0.80 | 97.97 | | | |
| 0.0039 | 0.0025 | 0.96 | 98.93 | | | |
| 0.0031 | 0.0028 | 1.07 | 100.00 | | | |
| total | 0.2613 | 100.00 | | | | |

TABLE 9

Excel DATA1.126 (Batch 22)

| PORE DIAMETER μm | Incremental Intrusion mL/g | Incremental Intrusion Percent | Cummulative Intrusion Percent | PORE DIAMETER μm | Incremental Intrusion mL/g | Incremental Intrusion Percent |
|---|---|---|---|---|---|---|
| 300 | 0 | 0.00 | 0.00 | | | |
| 179.835 | 0.0005 | 0.22 | 0.22 | | | |
| 144.5144 | 0.0003 | 0.13 | 0.34 | | | |
| 118.8772 | 1E-04 | 0.04 | 0.39 | | | |
| 85.9364 | 0.0003 | 0.13 | 0.52 | | | |
| 67.2501 | 0.0004 | 0.17 | 0.69 | | | |
| 51.7356 | 0.0003 | 0.13 | 0.82 | | | |
| 40.3645 | 0 | 0.00 | 0.82 | | | |
| 31.4021 | 0.0001 | 0.04 | 0.86 | | | |
| 24.5747 | 0.0002 | 0.09 | 0.95 | | | |
| 19.1522 | −0.0001 | −0.04 | 0.90 | | | |
| 14.9049 | 0.0001 | 0.04 | 0.95 | | | |
| 12.3548 | 0.0003 | 0.13 | 1.08 | | | |
| 9.0401 | 0.0002 | 0.09 | 1.16 | | | |
| 7.0369 | −0.0002 | −0.09 | 1.08 | | | |
| 6.0369 | 0.0004 | 0.17 | 1.25 | | | |
| 4.2819 | 0.0004 | 0.17 | 1.42 | | | |
| 3.3411 | 0.0013 | 0.56 | 1.98 | 3.3411 | 0.0013 | 0.56 |
| 2.5936 | 0.0017 | 0.73 | 2.71 | 2.5936 | 0.0017 | 0.73 |
| 2.0211 | 0.003 | 1.29 | 4.00 | 2.0211 | 0.003 | 1.29 |
| 1.5729 | 0.0049 | 2.11 | 6.11 | 1.5729 | 0.0049 | 2.11 |
| 1.2222 | 0.0058 | 2.50 | 8.61 | 1.2222 | 0.0058 | 2.50 |
| 0.9503 | 0.0068 | 2.93 | 11.54 | 0.9503 | 0.0068 | 2.93 |
| 0.7426 | 0.0065 | 2.80 | 14.33 | 0.7426 | 0.0065 | 2.80 |
| 0.5763 | 0.007 | 3.01 | 17.35 | 0.5763 | 0.007 | 3.01 |
| 0.4497 | 0.0065 | 2.80 | 20.15 | 0.4497 | 0.0065 | 2.80 |
| 0.3491 | 0.0058 | 2.50 | 22.64 | 0.3491 | 0.0058 | 2.50 |
| 0.2721 | 0.0046 | 1.98 | 24.62 | 0.2721 | 0.0046 | 1.98 |
| 0.2125 | 0.0045 | 1.94 | 26.56 | 0.2125 | 0.0045 | 1.94 |
| 0.1629 | 0.0059 | 2.54 | 29.10 | 0.1629 | 0.0059 | 2.54 |
| 0.128 | 0.0113 | 4.86 | 33.96 | 0.128 | 0.0113 | 4.86 |
| 0.1004 | 0.022 | 9.47 | 43.44 | 0.1004 | 0.022 | 9.47 |
| 0.0782 | 0.0283 | 12.18 | 55.62 | total | 0.0976 | 42.01 |
| 0.0628 | 0.0262 | 11.28 | 66.90 | | | |
| 0.0606 | 0.0006 | 0.26 | 67.15 | double check | 42.01 | 42.01 |
| 0.0474 | 0.025 | 10.76 | 77.92 | | | |
| 0.0369 | 0.0162 | 6.97 | 84.89 | answer is | 42.01 | |
| 0.0313 | 0.0064 | 2.76 | 87.65 | | | |
| 0.0287 | 0.003 | 1.29 | 88.94 | | | |
| 0.0223 | 0.0106 | 4.56 | 93.50 | | | |
| 0.0174 | 0.0039 | 1.68 | 95.18 | | | |
| 0.0136 | 0.0048 | 2.07 | 97.24 | | | |
| 0.0106 | 0.0016 | 0.69 | 97.93 | | | |
| 0.0082 | 0.0017 | 0.73 | 98.67 | | | |

TABLE 9-continued

Excel DATA1.126 (Batch 22)

| PORE DIAMETER μm | Incremental Intrusion mL/g | Incremental Intrusion Percent | Cummulative Intrusion Percent | PORE DIAMETER μm | Incremental Intrusion mL/g | Incremental Intrusion Percent |
|---|---|---|---|---|---|---|
| 0.0064 | 0.0012 | 0.52 | 99.18 | | | |
| 0.005 | 0.0006 | 0.26 | 99.44 | | | |
| 0.0039 | 0.0006 | 0.26 | 99.70 | | | |
| 0.0031 | 0.0007 | 0.30 | 100.00 | | | |
| total | 0.2323 | 100.00 | | | | |

TABLE 10

Excel DATA1.128

| PORE DIAMETER μm | Incremental Intrusion mL/g | Incremental Intrusion Percent | Cummulative Intrusion Percent | PORE DIAMETER μm | Incremental Intrusion mL/g | Incremental Intrusion Percent |
|---|---|---|---|---|---|---|
| 300 | 0 | 0.00 | 0.00 | | | |
| 178.9773 | 0.0004 | 0.17 | 0.17 | | | |
| 144.1443 | 0.0006 | 0.25 | 0.42 | | | |
| 120.2743 | 0 | 0.00 | 0.42 | | | |
| 85.8054 | 0.0005 | 0.21 | 0.63 | | | |
| 67.3306 | 0.0001 | 0.04 | 0.67 | | | |
| 51.7594 | 0 | 0.00 | 0.67 | | | |
| 40.2635 | 0.0003 | 0.13 | 0.80 | | | |
| 31.3322 | 0.0006 | 0.25 | 1.05 | | | |
| 24.564 | 0.0006 | 0.25 | 1.31 | | | |
| 19.1294 | −0.0005 | −0.21 | 1.10 | | | |
| 14.901 | −0.0017 | −0.72 | 0.38 | | | |
| 12.3575 | 0.0002 | 0.08 | 0.46 | | | |
| 9.0423 | 0.0014 | 0.59 | 1.05 | | | |
| 7.0172 | 0.0021 | 0.88 | 1.94 | | | |
| 6.0366 | −0.0007 | −0.29 | 1.64 | | | |
| 4.2818 | 0.001 | 0.42 | 2.06 | | | |
| 3.3315 | 0.0019 | 0.80 | 2.87 | 3.3315 | 0.0019 | 0.80 |
| 2.5913 | 0.0031 | 1.31 | 4.17 | 2.5913 | 0.0031 | 1.31 |
| 2.0198 | 0.0046 | 1.94 | 6.11 | 2.0198 | 0.0046 | 1.94 |
| 1.5714 | 0.0063 | 2.65 | 8.77 | 1.5714 | 0.0063 | 2.65 |
| 1.2171 | 0.0083 | 3.50 | 12.26 | 1.2171 | 0.0083 | 3.50 |
| 0.9475 | 0.0084 | 3.54 | 15.80 | 0.9475 | 0.0084 | 3.54 |
| 0.7399 | 0.0077 | 3.24 | 19.05 | 0.7399 | 0.0077 | 3.24 |
| 0.5758 | 0.0064 | 2.70 | 21.74 | 0.5758 | 0.0064 | 2.70 |
| 0.45 | 0.0048 | 2.02 | 23.77 | 0.45 | 0.0048 | 2.02 |
| 0.3499 | 0.0042 | 1.77 | 25.54 | 0.3499 | 0.0042 | 1.77 |
| 0.2726 | 0.0036 | 1.52 | 27.05 | 0.2726 | 0.0036 | 1.52 |
| 0.2126 | 0.0035 | 1.47 | 28.53 | 0.2126 | 0.0035 | 1.47 |
| 0.163 | 0.0044 | 1.85 | 30.38 | 0.163 | 0.0044 | 1.85 |
| 0.1284 | 0.007 | 2.95 | 33.33 | 0.1284 | 0.007 | 2.95 |
| 0.1002 | 0.016 | 6.74 | 40.08 | 0.1002 | 0.016 | 6.74 |
| 0.0781 | 0.0254 | 10.70 | 50.78 | total | 0.0902 | 38.01 |
| 0.0627 | 0.0256 | 10.79 | 61.57 | | | |
| 0.0605 | 0.0008 | 0.34 | 61.90 | double check | 38.01 | 38.01 |
| 0.0474 | 0.0285 | 12.01 | 73.91 | | | |
| 0.0369 | 0.0187 | 7.88 | 81.80 | answer is | 38.01 | |
| 0.0313 | 0.004 | 1.69 | 83.48 | | | |
| 0.0287 | 0.0047 | 1.98 | 85.46 | | | |
| 0.0224 | 0.0141 | 5.94 | 91.40 | | | |
| 0.0174 | 0.0062 | 2.61 | 94.02 | | | |
| 0.0136 | 0.0053 | 2.23 | 96.25 | | | |
| 0.0106 | 0.0028 | 1.18 | 97.43 | | | |
| 0.0082 | 0.002 | 0.84 | 98.27 | | | |
| 0.0064 | 0.0013 | 0.55 | 98.82 | | | |
| 0.005 | 0.001 | 0.42 | 99.24 | | | |
| 0.0039 | 0.0008 | 0.34 | 99.58 | | | |
| 0.0031 | 0.001 | 0.42 | 100.00 | | | |
| total | 0.2373 | 100.00 | | | | |

TABLE 11

Excel DATA1.127 (Batch 25)

| PORE DIAMETER μm | Incremental Intrusion mL/g | Incremental Intrusion Percent | Cummulative Intrusion Percent | PORE DIAMETER μm | Incremental Intrusion mL/g | Incremental Intrusion Percent |
|---|---|---|---|---|---|---|
| 300 | 0 | 0.00 | 0.00 | | | |
| 178.9773 | 0.0003 | 0.10 | 0.10 | | | |
| 144.1443 | 0.0004 | 0.13 | 0.22 | | | |
| 120.2743 | 0 | 0.00 | 0.22 | | | |
| 85.8054 | 0.0007 | 0.22 | 0.45 | | | |
| 67.3306 | 0.0004 | 0.13 | 0.58 | | | |
| 51.7594 | 0.0006 | 0.19 | 0.77 | | | |
| 40.2635 | 0.0003 | 0.10 | 0.87 | | | |
| 31.3322 | 0.0002 | 0.06 | 0.93 | | | |
| 24.564 | −1E-04 | −0.03 | 0.90 | | | |
| 19.1294 | 0.0004 | 0.13 | 1.03 | | | |
| 14.901 | 0.0011 | 0.35 | 1.38 | | | |
| 12.3575 | 0.0004 | 0.13 | 1.51 | | | |
| 9.0423 | 0.0003 | 0.10 | 1.60 | | | |
| 7.0172 | 0.0005 | 0.16 | 1.76 | | | |
| 6.0366 | 0.0015 | 0.48 | 2.24 | | | |
| 4.2595 | 0 | 0.00 | 2.24 | | | |
| 3.3178 | 0.0016 | 0.51 | 2.76 | 3.3178 | 0.0016 | 0.51 |
| 2.5829 | 0.0036 | 1.15 | 3.91 | 2.5829 | 0.0036 | 1.15 |
| 2.0148 | 0.0065 | 2.08 | 5.99 | 2.0148 | 0.0065 | 2.08 |
| 1.5685 | 0.0086 | 2.76 | 8.75 | 1.5685 | 0.0086 | 2.76 |
| 1.2153 | 0.011 | 3.53 | 12.28 | 1.2153 | 0.011 | 3.53 |
| 0.9466 | 0.0105 | 3.37 | 15.64 | 0.9466 | 0.0105 | 3.37 |
| 0.7394 | 0.0097 | 3.11 | 18.75 | 0.7394 | 0.0097 | 3.11 |
| 0.5755 | 0.0086 | 2.76 | 21.51 | 0.5755 | 0.0086 | 2.76 |
| 0.4498 | 0.0071 | 2.28 | 23.78 | 0.4498 | 0.0071 | 2.28 |
| 0.3498 | 0.0062 | 1.99 | 25.77 | 0.3498 | 0.0062 | 1.99 |
| 0.2725 | 0.0057 | 1.83 | 27.60 | 0.2725 | 0.0057 | 1.83 |
| 0.2125 | 0.0069 | 2.21 | 29.81 | 0.2125 | 0.0069 | 2.21 |
| 0.163 | 0.01 | 3.21 | 33.01 | 0.163 | 0.01 | 3.21 |
| 0.1284 | 0.015 | 4.81 | 37.82 | 0.1284 | 0.015 | 4.81 |
| 0.1002 | 0.0249 | 7.98 | 45.80 | 0.1002 | 0.0249 | 7.98 |
| 0.0781 | 0.0293 | 9.39 | 55.19 | total | 0.1359 | 43.56 |
| 0.0627 | 0.0288 | 9.23 | 64.42 | | | |
| 0.0605 | 0.0011 | 0.35 | 64.78 | double check | 43.56 | 43.56 |
| 0.0474 | 0.0321 | 10.29 | 75.06 | | | |
| 0.0369 | 0.02 | 6.41 | 81.47 | answer is | 43.56 | |
| 0.0313 | 0.0053 | 1.70 | 83.17 | | | |
| 0.0287 | 0.005 | 1.60 | 84.78 | | | |
| 0.0224 | 0.0149 | 4.78 | 89.55 | | | |
| 0.0174 | 0.007 | 2.24 | 91.79 | | | |
| 0.0136 | 0.0057 | 1.83 | 93.62 | | | |
| 0.0106 | 0.0042 | 1.35 | 94.97 | | | |
| 0.0082 | 0.003 | 0.96 | 95.93 | | | |
| 0.0064 | 0.0037 | 1.19 | 97.12 | | | |
| 0.005 | 0.0027 | 0.87 | 97.98 | | | |
| 0.0039 | 0.0031 | 0.99 | 98.97 | | | |
| 0.0031 | 0.0032 | 1.03 | 100.00 | | | |
| total | 0.312 | 100.00 | | | | |

Each of the catalysts of Examples 2–9 was performance tested in a fixed bed maleic anhydride reactor at a standardized set of reaction conditions—2.4±0.2 mole % n-butane in synthetic air (21 mol % oxygen/71 mol % helium, 1.034× $10^2$ kPa-g (15.0 psig) inlet pressure, and 1500 GHSV. The catalyst (11.7 g) was charged to a 1.092 cm inside diameter ×30.48 cm long (0.43 inch inside diameter by 1' long) reactor to provide a catalyst bed of approximately 15.24 cm (6") in length. The catalyst was run for a period of time from about 20 hours to about 100 hours unless otherwise indicated at the standardized performance test conditions prior to determining the reaction (bath) temperature and reaction yield. The reaction (bath) temperature and maximum yield were determined for each catalyst when the catalyst was running at 85±2 mol % n-butane conversion. The parameters and results are tabulated in Table 12.

TABLE 12

| EXAMPLE | ANST BATCH | TIME (HOURS) | BATH (°C.) | CONV (%) | FCY² (%) | BCY¹ (%) | BCY AT 85% (%) | CTOT³ (%) | AVG. STAND. BATH (°C.) | AVG. STAND. YIELD (%) | YIELD DELTA (%) | VOX |
|---|---|---|---|---|---|---|---|---|---|---|---|---|
| 2 | 6 | 108 | 411 | 84.8 | 59.1 | 60.1 | 60.2 | 98.0 | 421 | 56.6 | 3.7 | 4.21 |
| 2 | 6 | 138 | 411 | 85.3 | 59.7 | 59.5 | 59.3 | 99.2 | 421 | 56.6 | 2.7 | 4.21 |
| 3 | 7 | 87 | 423 | 85.0 | 58.5 | 58.1 | 58.1 | 99.3 | 421 | 56.6 | 1.5 | 4.14 |
| 3 | 7 | 124 | 419 | 84.9 | 56.4 | 57.6 | 57.7 | 97.8 | 421 | 56.6 | 1.1 | 4.14 |
| 3 | 7 | 101 | 424 | 85.2 | 56.3 | 57.0 | 56.9 | 98.3 | 421 | 56.6 | 0.3 | 4.14 |
| 4 | 9 | 84 | 430 | 85.0 | 56.5 | 56.2 | 56.2 | 99.2 | 421 | 56.6 | -0.4 | 4.19 |
| 4 | 9 | 83 | 413 | 85.3 | 58.8 | 58.7 | 58.5 | 99.2 | 421 | 56.6 | 1.9 | 4.19 |
| 4 | 9 | 102 | 423 | 85.5 | 57.2 | 57.8 | 57.5 | 98.4 | 421 | 56.6 | 0.9 | 4.19 |
| 5 | 21 | 92 | 411 | 85.5 | 56.9 | 61.4 | 61.0 | 94.5 | 420 | 57.5 | 3.5 | 4.16 |
| 6 | 22 | 101 | 411 | 85.2 | 58.0 | 59.4 | 59.3 | 97.6 | 420 | 57.5 | 1.7 | 4.16 |
| 7 | 23 | 108 | 411 | 85.2 | 59.7 | 61.1 | 61.0 | 97.5 | 420 | 57.5 | 3.4 | 4.18 |
| 8 | 24 | 97 | 418 | 85.5 | 58.5 | 59.6 | 59.3 | 97.9 | 420 | 57.5 | 1.7 | 4.18 |
| 9 | 25 | 95 | 413 | 85.5 | 59.8 | 60.1 | 59.7 | 98.7 | 420 | 57.5 | 2.2 | 4.17 |
| Average | | | 416.8 | 85.2 | 58.1 | 59.0 | 58.8 | 98.1 | 420.6 | 56.9 | 1.88 | 4.17 |
| Standard Deviation | | | 6.24 | 0.23 | 1.26 | 1.51 | 1.45 | 1.22 | 0.88 | 0.47 | 1.19 | 0.02 |

¹% BCY (% Back Calculated Yield) and Bath Actvity Temperature (°C. required to give 85 +/− 1% butane concentration) were obtained from microreactors running at 1500 GHSV, 15 psig, and 2.4 mole % butane.
²(Moles maleic produced/moles n-butane feed) (100%)
³Closure of carbon balance

EXAMPLE 10

Figure 6:
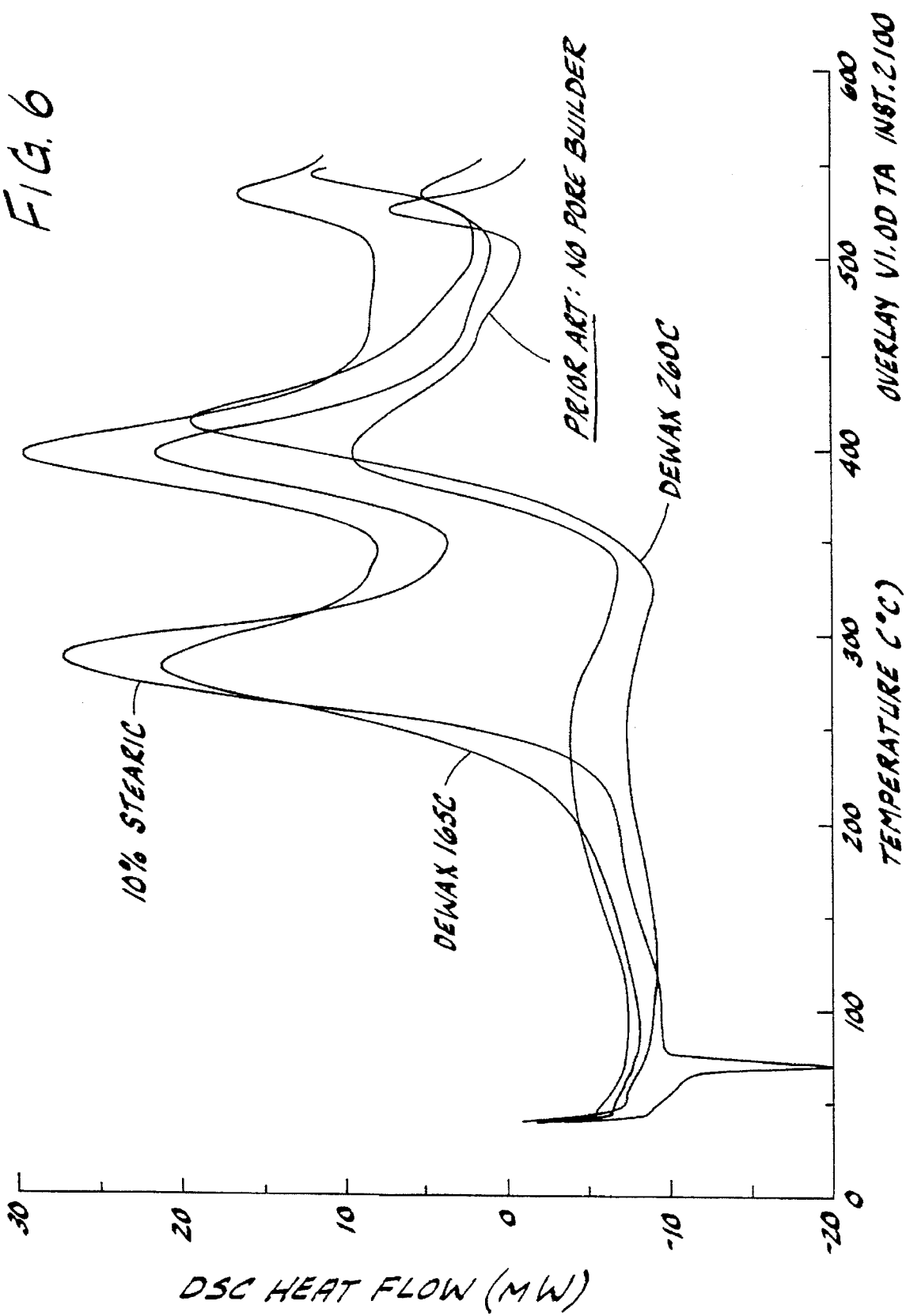
FIG. 6 is an overlay of several differential scanning calorimetry curves, one for a tabletted vanadium/phosphorus/oxide catalyst precursor composition prepared in accordance with the invention, the others for tabletted precursors prepared without a pore builder or with inadequate removal of the pore builder prior to differential scanning calorimetry.

Differential scanning calorimetry tests were conducted after conclusion of the pore builder removal step on catalyst precursor bodies prepared in the essentially the same manner as the precursor bodies of Examples 1–9. For purposes of comparison, additional differential scanning calorimetry tests were conducted on catalyst precursor bodies prepared in the essentially the same manner except that the pore builder removal step was terminated after at least 16 hours at 165° C.; and further tests were conducted on a catalyst of the prior art which had been produced without the use of any pore builder. The results of these tests are illustrated in the DSC readout plot of FIG. 6.

In view of the above, it will be seen that the several objects of the invention are achieved and other advantageous results attained.

As various changes could be made in the above compositions and processes without departing from the scope of the invention, it is intended that all matter contained in the above description and shown in the accompanying drawings shall be interpreted as illustrative and not in a limiting sense.

What is claimed is:

1. An activated porous phosphorus/vanadium oxide catalyst adapted for the catalytic oxidation of a hydrocarbon to produce a carboxylic acid anhydride, said catalyst comprising a shaped body having a volume of at least about 0.02 cc, a phosphorus/vanadium atom ratio of from about 1.05 to about 1.20, a B.E.T. surface area of at least about 15 m²/g, an average vanadium oxidation state of between about 4.06 and about 4.3, a total pore volume of at least about 0.15 cc/g, a normalized apparent shaped body density of between about 1.0 and about 2.0 g/cc, and a crush strength of at least about 4 pounds, between about 10% and about 20% of the pore volume of said catalyst being constituted of pores having a diameter between about 0.2 microns and about 2 microns, and at least about 40% of the pore volume being constituted of pores having a diameter of less than about 0.1 microns.

2. A catalyst as set forth in claim 1 wherein pores having a diameter between about 0.1 microns and about 3.3 microns constitute at least about 20% of the total pore volume of said catalyst.

3. A catalyst as set forth in claim 2 wherein pores having a diameter between about 0.1 microns and about 3.3 microns constitute between about 25% and about 60% of the total pore volume of said catalyst.

4. A catalyst as set forth in claim 3 wherein pores having a diameter between about 0.1 microns and about 3.3 microns constitute between about 30% and about 50% of the total pore volume of said catalyst.

5. A catalyst as set forth in claim 1 wherein pores having a diameter between about 0.5 and about 1.2 µM constitute between about 5% and about 20% of the total pore volume.

6. A catalyst as set forth in claim 5 wherein pores having a diameter between about 0.2 and about 2 µM constitute between about 12% and about 30% of the total pore volume of the catalyst, and pores having a diameter of between about 0.5 and about 1.2 µM constitute between about 7% and about 12% of the total pore volume.

7. A catalyst as set forth in claim 1 wherein pores having a diameter of less than about 0.1 microns constitute between about 40% and about 70% of the total pore volume of said catalyst.

8. A catalyst as set forth in claim 1 wherein said shaped body comprising said catalyst has exit holes having a diameter of at least 2 microns at the external surfaces thereof, said holes being present in a density of at least about 75 surface holes per mm², said holes being in communication with the body interior.

9. A catalyst as set forth in claim 1 wherein said shaped body comprises an opening therethrough for flow of reactant and product gases when the catalyst is used in the manufacture of maleic anhydride.

10. A catalyst as set forth in claim 9 wherein said shaped body comprise a cylinder having a bore therethrough.

11. A process for the preparation of a phosphorus/vanadium oxide catalyst comprising the steps of:
   preparing a modified catalyst precursor composition comprising a mixture of a particulate phosphorus/vanadium oxide catalyst precursor and a pore modification agent in proportions sufficient to provide a pore modification agent concentration of between about 8% and about 16% by weight, said pore modification agent being subject to vaporization, decomposition and/or oxidation at a temperature below 300° C. without leaving a substantial residue;

forming said modified catalyst precursor composition into a predetermined shape under compression, thereby producing a shaped porous catalyst precursor body comprising said catalyst precursor composition and containing said pore modification agent; and heating said precursor body while passing a stripping gas comprising air thereover for removal of at least about 80% by weight of said pore modification agent at a temperature not greater than about 300° C., said porous body being heated at a rate of between about 1° and about 3° C. per minute to a hold temperature that is below a threshold temperature at which the pore modification agent is subject to catalytic oxidation in the presence of the phosphorus/vanadium oxide catalyst precursor, said porous body being further heated above said hold temperature, the rate of heating being between about 0.5° C. and about 2° C. per hour in a temperature range of between about 15° C. and about 40° C. above said hold temperature.

12. A process for the preparation of a phosphorus/vanadium oxide catalyst comprising the steps of:

preparing a modified catalyst precursor composition comprising a mixture of a particulate phosphorus/vanadium oxide catalyst precursor and a volatile pore modification agent in proportions sufficient to provide a pore modification agent concentration of between about 8% and about 16% by weight, said pore modification agent having a vapor pressure of at least about 1 mm Hg at a temperature between about 150° C. and about 250° C. and being subject to vaporization, decomposition and/or oxidation at a temperature below 300° C. without leaving a substantial residue;

forming said modified catalyst precursor composition into a predetermined shape under compression, thereby producing a shaped porous catalyst precursor body comprising said catalyst precursor composition and containing said volatile pore modification agent;

heating said catalyst precursor body while passing a stripping gas comprising air thereover at a linear rate of at least about 25 cm/sec. for removal of at least about 80% by weight of said volatile pore modification agent at a temperature not greater than about 300° C., said porous body being heated at a rate of between about 1° and about 3° C. per minute to a hold temperature that is below a threshold temperature at which the pore modification agent is subject to catalytic oxidation in the presence of the phosphorus/vanadium oxide catalyst precursor; and heating the shaped body from said hold temperature to a terminal temperature at which the concentration of residual pore builder in the shaped body has been reduced to a terminal level, the terminal level being defined as a concentration of residual pore modification agent which does not result in an exotherm that adversely alters the catalyst structure upon subsequent transformation of the precursor composition to active catalyst by heat treatment of the shaped body in the presence of air, steam or nitrogen under reference conditions, such reference conditions comprising heating said precursor at a rate of 1.8° C. per minute between 300° C. and 400° C.

13. A process as set forth in claim 12 wherein said shaped porous body is heated to a temperature between about 150° C. and about 250° C. for removal of said pore modification agent.

14. A process as set forth in claim 12 wherein said pore modification agent substantially comprises stearic acid, and said hold temperature is between about 160° C. and about 170° C.

15. A process as set forth in claim 12 wherein said shaped body is heated from said hold temperature at a rate of between about 0.5° C. and about 2° C. per hour in a temperature range between about 15° C. and 40° C. above the hold temperature.

16. A process as set forth in claim 15 wherein said shaped body is heated at a rate of between about 10° C. and about 40° C. per minute between a temperature of about 200° C. and said terminal temperature.

17. A process as set forth in claim 16 wherein said terminal temperature is between about 240° C. and about 260° C.

18. A process as set forth in claim 17 wherein said shaped body is cooled from said terminal temperature to ambient temperature within about 0.5 to about 2 hours.

19. A process as set forth in claim 12 wherein said pore modification agent is removed by vaporization.

20. A process as set forth in claim 19 wherein said pore modification agent has a vapor pressure of at least about 1 mm Hg at a temperature below 300° C., and said agent is removed by passing a stripping gas over said catalyst body at a temperature at which said vapor pressure is at least about 1 mm Hg.

21. A process as set forth in claim 12 wherein essentially complete removal of said pore modification agent is provided, without reduction of vanadium in said precursor composition to an average oxidation state of less than about 3.8.

22. A process as set forth in claim 21 wherein said pore modification agent has a vapor pressure of at least about 1 mm Hg at a temperature below the temperature at which oxygen atoms in said precursor composition are labile and subject to abstraction.

23. A process as set forth in claim 12 wherein said pore modification agent is selected from the group consisting of fatty acids, fatty acid esters, and polynuclear organic compounds.

24. A process as set forth in claim 12 wherein said particulate phosphorus/vanadium oxide precursor is mixed with a particulate pore modification agent, the mean particle diameter of said pore modification agent being not greater than about two orders of magnitude different from the mean particle diameter of said precursor.

25. A process as set forth in claim 24 wherein said pore modification agent has a mean particle diameter of between about 10 and about 500 microns.

26. A process as set forth in claim 25 wherein said pore modification agent has a mean particle diameter of between about 30 and about 90 microns.

27. A process as set forth in claim 26 wherein said particulate phosphorus/vanadium oxide precursor has a mean particle diameter of between about 20 and about 200 microns.

28. A process as set forth in claim 12 wherein, after removal of said pore modification agent, said precursor body is heated at a temperature above 300° C. to transform said precursor body to a phosphorus/vanadium oxide catalyst body active for the oxidation of a hydrocarbon to maleic anhydride.

29. A process as set forth in claim 28 wherein transformation of said precursor body to an active catalyst body comprises the steps of:

(a) heating the precursor body in an atmosphere selected from the group consisting of air, steam, inert gas, and mixtures thereof to a temperature not to exceed about 300° C., thereby removing said pore modification agent from said catalyst precursor body substantially at a temperature below 300° C., to produce a catalyst precursor body having a pore volume of at least about 0.15 cc/g, at least about 25% of the pore volume of said catalyst being constituted of pores having a diameter between about 0.1 microns and about 3.3 microns, and at least about 40% of the pore volume being constituted of pores having a diameter of less than about 0.1 microns;

(b) maintaining the catalyst precursor body at the temperature of Step (a) and providing an atmosphere containing molecular oxygen, steam, and optionally an inert gas, the atmosphere being represented by the formula $$(O_2)_x(H_2O)_y(IG)_z$$

wherein IG is an inert gas and x, y, and z represent mol percent of the $O_2$, $H_2O$, and IG components, respectively, in the molecular oxygen/steam-containing atmosphere, with x having a value greater than zero (0) mol %, but less than 100 mol %, y having a value greater than zero (0) mol %, but less than 100 mol %, and z having a value representing the balance of the molecular oxygen/steam-containing atmosphere;

(c) increasing the temperature of the catalyst precursor at a programmed rate of from about 2° C./min to about 12° C./min to a value effective to eliminate the water of hydration from the catalyst precursor body;

(d) adjusting the temperature from Step (c) to a value greater than 350° C., but less than 550° C., and maintaining the adjusted temperature in the molecular oxygen/steam-containing atmosphere for a time effective to provide a vanadium oxidation state of from about +4.06 to about +4.3; and (e) continuing to maintain the adjusted temperature in a nonoxidizing, steam-containing atmosphere for a time effective to complete the catalyst precursor-to-active catalyst transformation to yield the active catalyst.

30. A process as set forth in claim 29 wherein said precursor composition corresponds to the formula $$VO(M)_m HPO_4 \bullet aH_2O \bullet b(P_{2/c}O) \bullet n(organics)$$

wherein M is at least one promoter element selected from the group consisting of elements from Groups IA, IB, IIA, IIB, IIIA, IIIB, IVA, IVB, VA, VB, VIA, VIB, and VIIIA of the Periodic Table of the Elements, and mixtures thereof, m is a number from zero (0) to about 0.2, a is a number of at least about 0.5, b is a number taken to provide a P/V atom ratio of from about 1.0 to about 1.3, c is a number representing the oxidation number of phosphorus and has a value of 5, and n is a number taken to represent the weight % of intercalated organics component, and said precursor is transformed into an active catalyst represented by the formula $$(VO)_2(M)_m P_2O_7 \bullet b(P_{2/c}O)$$

wherein M, m, b, and c are as defined above.

31. A process as set forth in claim 29 wherein transformation of said precursor to said active catalyst is carried out after removal of said pore modification agent from said catalyst precursor body.

32. A process as set forth in claim 29 wherein residual said pore modification agent is removed during Step (c) of said transformation.

33. A process as set forth in claim 29 wherein said catalyst precursor body is heated in the presence of said stripping gas until an end point at which at least about 80% of said pore modification agent has been removed from said body, the terminal temperature of said catalyst precursor body at said end point being at least 200° C., and said body is not cooled below about 100° C. during the period after said end point and prior to Step (a) of the transformation of said precursor body to an active catalyst.

34. A process as set forth in claim 33 wherein said catalyst body is not cooled by more than 50° C. below said terminal temperature after said end point and prior to said Step (a).

35. A process as set forth in claim 29 in which the pore modification agent is removed from said catalyst precursor body by passing said stripping gas over said catalyst precursor body in an oven, and transformation of said catalyst precursor body to active catalyst precursor is carried out in the same oven without removal of the catalyst precursor body from the oven in the period between the end point of the pore modification agent removal step and said Step (a).

* * * * *

UNITED STATES PATENT AND TRADEMARK OFFICE
CERTIFICATE OF CORRECTION

PATENT NO. : 5,641,722
DATED : June 24, 1997
INVENTOR(S) : Scott F. Mitchell, et al.

It is certified that error appears in the above-indentified patent and that said Letters Patent is hereby corrected as shown below:

Column 39, claim 1, line 58, "20%" should read ---40%---.

Signed and Sealed this

Twenty-first Day of October 1997

Attest:

Attesting Officer

BRUCE LEHMAN

Commissioner of Patents and Trademarks